(12) United States Patent
Zheng et al.

(10) Patent No.: US 10,464,927 B2
(45) Date of Patent: Nov. 5, 2019

(54) 2,4-DISUBSTITUTED PYRIMIDINES AS CDK INHIBITORS

(71) Applicant: Shanghai Xunhe Pharmaceutical Technology Co. Ltd., Shanghai (CN)

(72) Inventors: Yongyong Zheng, Shanghai (CN); Hua Jin, Shanghai (CN); Feng Zhou, Shanghai (CN); Meihua Huang, Shanghai (CN); Xin Meng, Beijing (CN)

(73) Assignee: Shanghai Xunhe Pharmaceutical Technology Co. Ltd., Shanghai (CN)

( * ) Notice: Subject to any disclaimer, the term of this patent is extended or adjusted under 35 U.S.C. 154(b) by 0 days.

(21) Appl. No.: 16/155,861

(22) Filed: Oct. 9, 2018

(65) Prior Publication Data

US 2019/0071427 A1  Mar. 7, 2019

Related U.S. Application Data

(63) Continuation of application No. PCT/CN2017/078933, filed on Mar. 31, 2017.

(30) Foreign Application Priority Data

Apr. 11, 2016 (CN) .......................... 2016 1 0220246

(51) Int. Cl.
*A61K 31/505* (2006.01)
*C07D 239/42* (2006.01)
*C07D 401/14* (2006.01)
*C07D 473/00* (2006.01)
*C07D 487/04* (2006.01)
*A61P 35/00* (2006.01)
*C07D 471/04* (2006.01)

(52) U.S. Cl.
CPC ............ *C07D 401/14* (2013.01); *A61P 35/00* (2018.01); *C07D 471/04* (2013.01); *C07D 473/00* (2013.01); *C07D 487/04* (2013.01)

(58) Field of Classification Search
CPC ........................... A61K 31/505; C07D 239/42
USPC ............................................ 514/275; 544/297
See application file for complete search history.

*Primary Examiner* — Douglas M Willis

(57) ABSTRACT

The present disclosure relates to a 2,4-disubstituted pyrimidine derivative and the use thereof as a therapeutically effective cyclin-dependent kinase (CDK) inhibitor. In particular, the present disclosure relates to the use of a new 2,4-disubstituted pyrimidine derivatives shown in formula (I) and a pharmaceutical composition thereof as a selective CDK4/6 inhibitor in preventing or treating diseases related to CDK4/6.

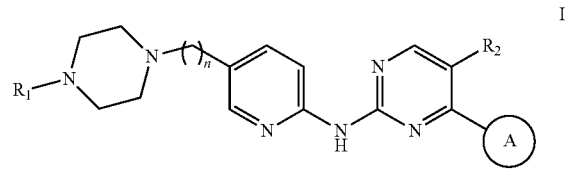

7 Claims, No Drawings

2,4-DISUBSTITUTED PYRIMIDINES AS CDK INHIBITORS

CROSS-REFERENCE TO RELATED APPLICATION

The present application is a continuation of international application No. PCT/CN2017/078933 filed on Mar. 31, 2017, which claims priority of Chinese patent application No. CN201610220246.9, filed on Apr. 11, 2016, which are hereby incorporated by reference in their entireties.

TECHNICAL FIELD

The disclosure relates to the technical field of pharmaceutical preparation, in particular to a 2,4-disubstituted pyrimidine derivative as a CDK inhibitor and a use thereof.

BACKGROUND

Cyclin-dependent kinase (CDK) and cyclin are important factors in the regulation of cell cycle. CDK can form a heterodimer with cyclin, wherein CDK is a catalytic subunit, cyclin is a regulatory subunit, and various cyclin-CDK complexes are formed, phosphorylating different substrates, thereby promoting and transforming the different phases of a cell cycle.

There are at least 9 CDKs in mammals. The transition from G1 phase to S phase in cells is mainly controlled by G1 phase CDK kinase. CDK kinases that bind to G1 cyclins mainly comprise CDK2, CDK4, and CKD6. Cyclin D mainly binds to CDK4 and CKD6 and regulates the activity of the latter; cyclin E binds to CDK2 at G1/S phase, exhibiting CDK2 kinase activity and promoting cell's entry into S phase. G2/M phase is mainly regulated by CDK1 kinase, Cyclin A and Cyclin B bind to CDK1, and CDK1 phosphorylates the substrate protein, such as histone H1 phosphorylation can cause chromosome condensation, or lamin phosphorylation can cause disintegration of nuclear membrane. During M phase, M-promoting factor (MPF) activates an anaphase-promoting complex APC, which is ubiquitously linked to Cyclin A and Cyclin B. With polyubiquitylation, they are degraded by a proteasome, which completes a cell cycle (Malumbres M. et al. Nat Cell Biol 11:1275, 2009; Malumbres M. et al. Nat Rev Cancer 9:153, 2009).

In the past decade, CDK inhibitors have been regarded as a hot spot for developing new anti-tumor drug in the global pharmaceutical industry, and more than 20 CDK inhibitors have entered clinical development. Although CDK inhibitors have significant preclinical anti-tumor pharmacodynamics, the results of most previous clinical trials were unsatisfactory. The main problems include lack of efficacy on solid tumors and the toxicity (Guha M. Nat Rev Drug Dis 11:892, 2012). During the analysis of serious toxic side effects, it was found that some CDK inhibitor drugs lack selectivity for CDK subtypes, resulting in greater side effects.

CDK4 and CDK6 are two closely related kinases that bind to Cyclin D during the tumor cell cycle and cause transition of G1 phase to S phase, which is essential for the cell cycle progression of DNA replication for cell division. Changes in the G1-S phase transition control mechanism through various genetic and biochemical adaptations have been found in more than 90% of human tumors. P16 and human retinoblastoma (Rb) are important tumor suppressor proteins that regulate cell cycle. P16 gene protein inhibits the feedback loop of CDK4, Cyclin D1 and Rb, and prevents the cell from hyperproliferation by regulating the protein activity of Rb for tumor suppression. It has been shown that activation of CDK4 and CDK6 causes changes in cell cycle in human tumors (such as breast tumor and myeloma). Inhibition of CDK4 and CDK6 can prevent inactivation of tumor suppressor protein Rb and interfere with tumor cell cycle progression (Choi Y J and Anders L, Oncogene 33:1890-903, 2014).

CDK4/6 plays a key role in the dysregulation of cell cycle control in various solid tumors and hematological tumors. There are several selective CDK4/6 inhibitors in clinical stages at present (e.g., Palbociclib, LY2835219, and LEE011). The clinical evaluation of these drugs also includes metastatic breast cancer, ovarian cancer, liposarcoma, non-small cell lung cancer, liver cancer, glioblastoma, melanoma, multiple myeloma and lymphoma and the like.

Although many CDK inhibitor compounds have been disclosed, a variety of drugs, particularly CDK4/6 inhibitors for treating CDK-related disorders are still needed due to CDK-mediated pathology.

SUMMARY

One of the objects of the present disclosure is to provide a novel 2,4-disubstituted pyrimidine derivative or a pharmaceutically acceptable salt thereof.

The second object of the present disclosure is to provide a use of the compound as a novel CDK4/6 inhibitor in the preparation of a medicament for the prevention or treatment of CDK4/6-related diseases. The various diseases caused by the imbalance of the cycle control involved with CDK4/6, especially malignant tumors to be treated include, but are not limited to breast cancer, ovarian cancer, prostate cancer, colorectal cancer, pancreatic cancer, liver cancer, melanoma, gastric cancer, and solid tumors and the like.

For above object, the present disclosure provides a 2,4-disubstituted pyrimidine derivative represented by the following Formula I or a pharmaceutically acceptable salt thereof:

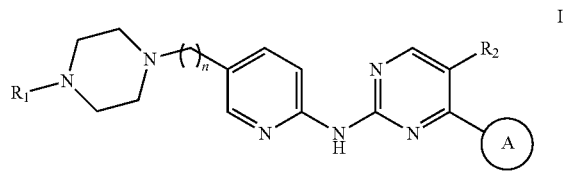

wherein, $R_1$ represents hydrogen, $C_1$-$C_3$ alkyl, or $C_3$-$C_7$ cycloalkyl;

$R_2$ represents hydrogen, halogen, methyl, methoxy, or trifluoromethyl;

n is 0 or 1;

Ring A is

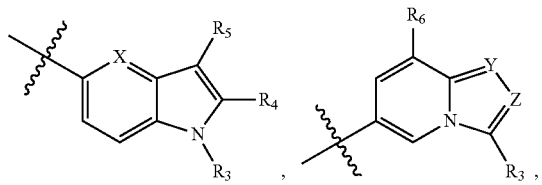

-continued

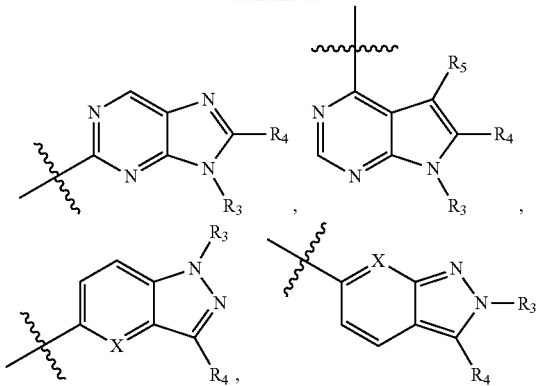

and when Ring A is

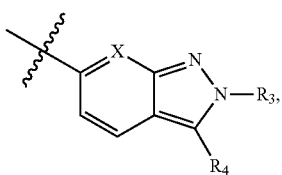

n is 0;

$R_3$ represents $C_1$-$C_5$ alkyl, or $C_3$-$C_7$ cycloalkyl;

$R_4$ and $R_5$ independently represents hydrogen, $C_1$-$C_3$ alkyl, $C_3$-$C_5$ cycloalkyl, acetyl, halogen, trifluoromethyl, cyano or $CONR_7R_8$;

$R_6$ represents hydrogen, or halogen;

$R_7$ and $R_8$ independently represents hydrogen or methyl;

X is $CR_6$ or N;

Y and Z are independently C or N.

The present disclosure also provides a pharmaceutical composition comprising at least one pharmaceutically acceptable carrier, and at least one compound of Formula (I) as described herein and a pharmaceutically acceptable salt thereof as a CDK4/6 inhibitor.

As used herein, "$C_1$-$C_3$ alkyl" refers to methyl, ethyl, n-propyl, or iso-propyl; "$C_1$-$C_5$ alkyl" refers to methyl, ethyl, n-propyl, iso-propyl, n-butyl, iso-butyl, sec-butyl, tert-butyl, 1-pentyl, 2-pentyl, 3-pentyl, 2-methyl-3-butyl, 1,1-dimethyl-1-propyl, 2,2-dimethyl-1-propyl; "halogen" refers to F, Cl, Br, I; "$C_3$-$C_7$ cycloalkyl" refers to cyclopropyl, cyclobutyl, cyclopentyl, cyclohexyl, cycloheptyl; and "$C_3$-$C_5$ cycloalkyl" refers to cyclopropyl, cyclobutyl, cyclopentyl.

Typical compounds of the present disclosure include but not limited to those in following Table 1:

TABLE 1

| Compound | Structure |
| --- | --- |
| I-1 | 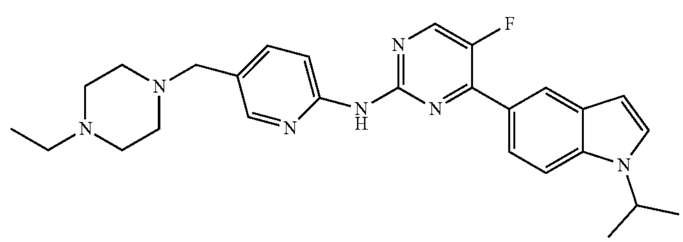 [SMILES: CCN1CCN(Cc2ccc(Nc3ncc(F)c(-c4ccc5c(ccn5C(C)C)c4)n3)nc2)CC1] |
| I-2 | 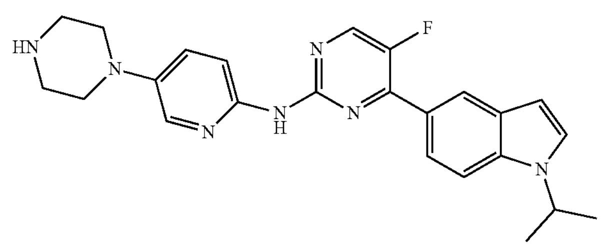 [SMILES: CC(C)n1ccc2cc(-c3nc(Nc4ccc(N5CCNCC5)cn4)ncc3F)ccc21] |
| I-3 | 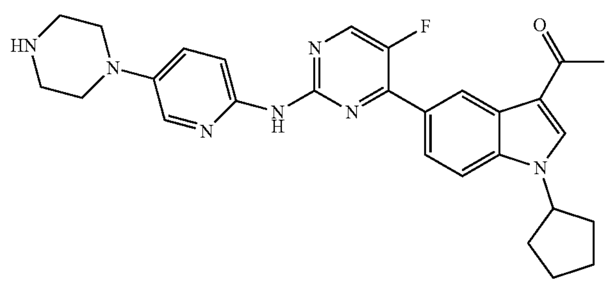 [SMILES: CC(=O)c1cn(C2CCCC2)c2ccc(-c3nc(Nc4ccc(N5CCNCC5)cn4)ncc3F)cc12] |

TABLE 1-continued

| Compound | Structure |
|---|---|
| I-4 | 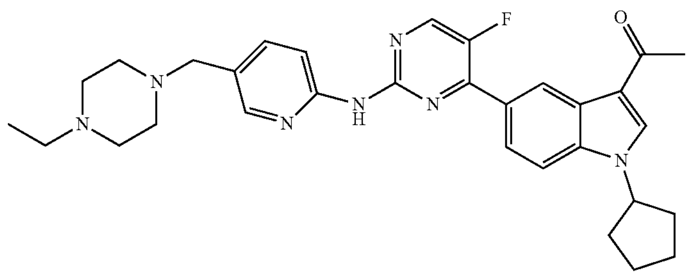 [SMILES: CCN1CCN(Cc2ccc(Nc3ncc(F)c(-c4ccc5c(c4)c(C(C)=O)cn5C4CCCC4)n3)nc2)CC1] |
| I-5 | 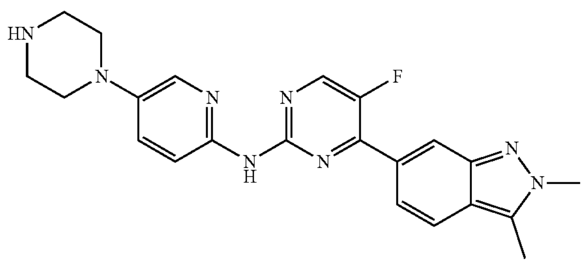 [SMILES: Cc1c2ccc(-c3nc(Nc4ccc(N5CCNCC5)cn4)ncc3F)cc2nn1C] |
| I-6 | 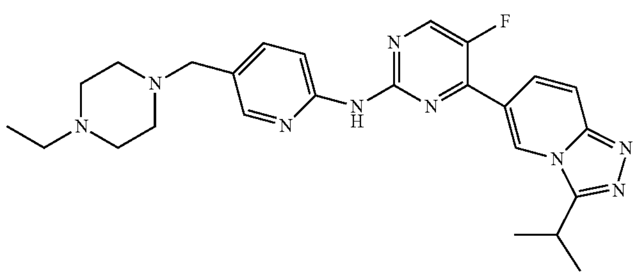 [SMILES: CCN1CCN(Cc2ccc(Nc3ncc(F)c(-c4ccc5nnc(C(C)C)n5c4)n3)nc2)CC1] |
| I-7 | 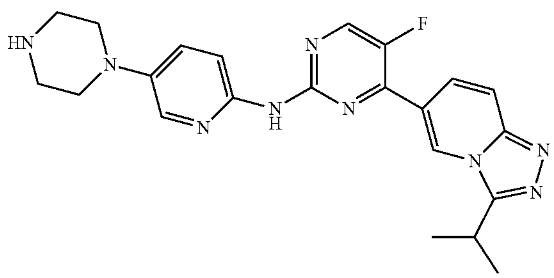 [SMILES: CC(C)c1nnc2ccc(-c3nc(Nc4ccc(N5CCNCC5)cn4)ncc3F)cn12] |
| I-8 | 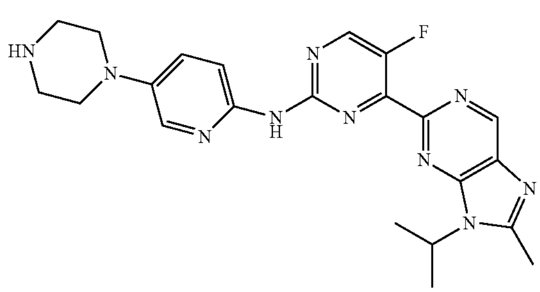 [SMILES: Cc1nc2cnc(-c3nc(Nc4ccc(N5CCNCC5)cn4)ncc3F)nc2n1C(C)C] |

TABLE 1-continued
| Compound | Structure |
|---|---|
| I-9 | 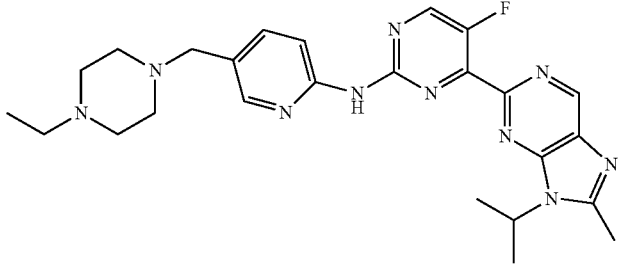 [SMILES: CCN1CCN(Cc2ccc(Nc3ncc(F)c(-c4ncc5nc(C)n(C(C)C)c5n4)n3)nc2)CC1] |
| I-10 | 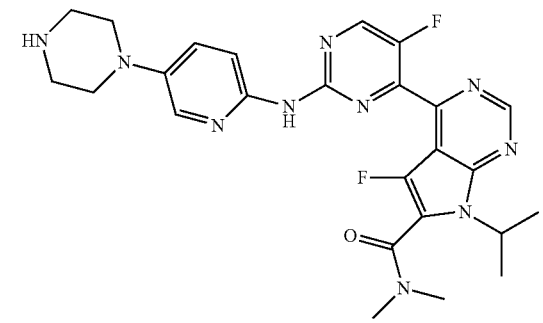 [SMILES: CC(C)n1c(C(=O)N(C)C)c(F)c2c(-c3nc(Nc4ccc(N5CCNCC5)cn4)ncc3F)ncnc21] |
| I-11 | 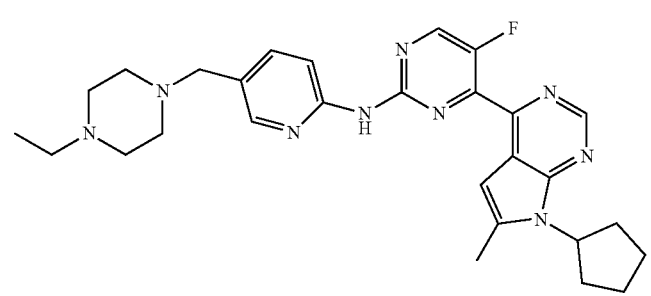 [SMILES: CCN1CCN(Cc2ccc(Nc3ncc(F)c(-c4ncnc5c4cc(C)n5C4CCCC4)n3)nc2)CC1] |
| I-12 | 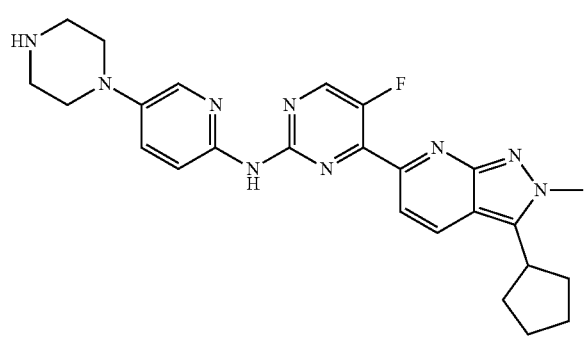 [SMILES: Cn1nc2nc(-c3nc(Nc4ccc(N5CCNCC5)cn4)ncc3F)ccc2c1C1CCCC1] |
| I-13 | 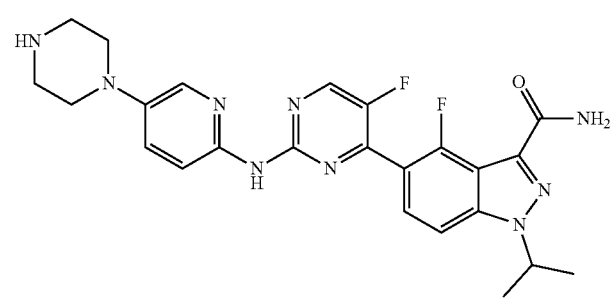 [SMILES: CC(C)n1nc(C(N)=O)c2c(F)c(-c3nc(Nc4ccc(N5CCNCC5)cn4)ncc3F)ccc21] |

TABLE 1-continued

| Compound | Structure |
|---|---|
| I-14 | 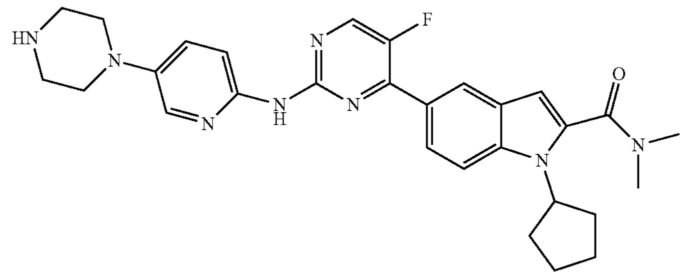 [SMILES: CN(C)C(=O)c1cc2cc(-c3nc(Nc4ccc(N5CCNCC5)cn4)ncc3F)ccc2n1C1CCCC1] |
| I-15 | 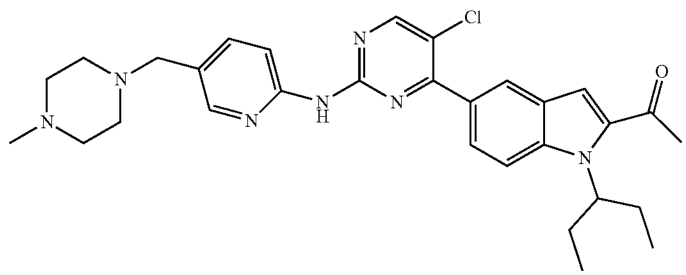 [SMILES: CCC(CC)n1c(C(C)=O)cc2cc(-c3nc(Nc4ccc(CN5CCN(C)CC5)cn4)ncc3Cl)ccc21] |
| I-16 | 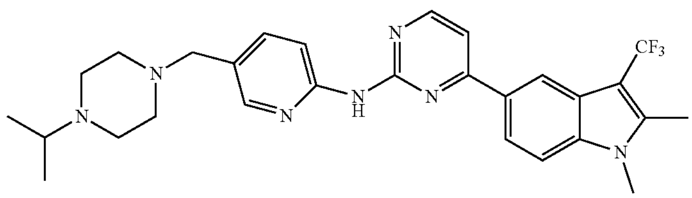 [SMILES: Cc1c(C(F)(F)F)c2cc(-c3ccnc(Nc4ccc(CN5CCN(C(C)C)CC5)cn4)n3)ccc2n1C] |
| I-17 | 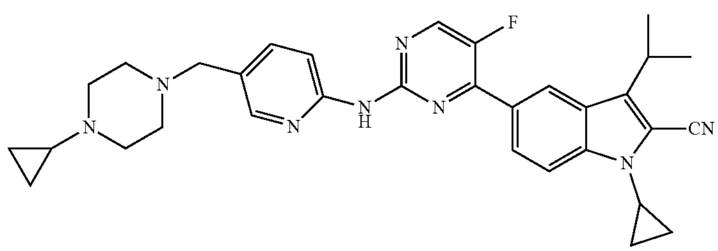 [SMILES: CC(C)c1c(C#N)n(C2CC2)c2ccc(-c3nc(Nc4ccc(CN5CCN(C6CC6)CC5)cn4)ncc3F)cc12] |
| I-18 | 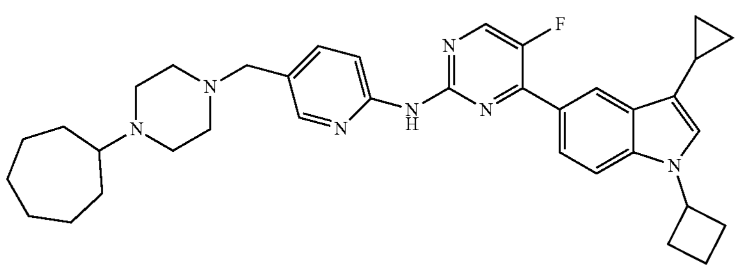 [SMILES: Fc1cnc(Nc2ccc(CN3CCN(C4CCCCCC4)CC3)cn2)nc1-c1ccc2c(c1)c(C1CC1)cn2C1CCC1] |
| I-19 | 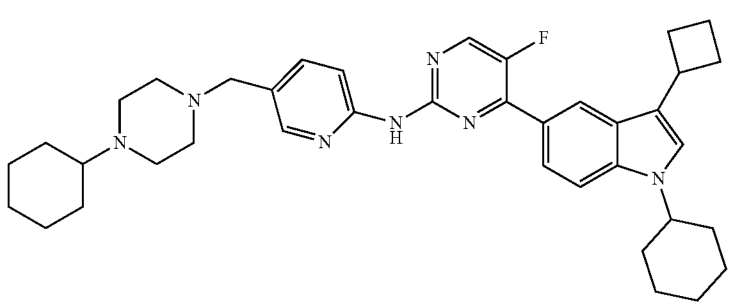 [SMILES: Fc1cnc(Nc2ccc(CN3CCN(C4CCCCC4)CC3)cn2)nc1-c1ccc2c(c1)c(C1CCC1)cn2C1CCCCC1] |

TABLE 1-continued
| Compound | Structure |
|---|---|
| I-20 | 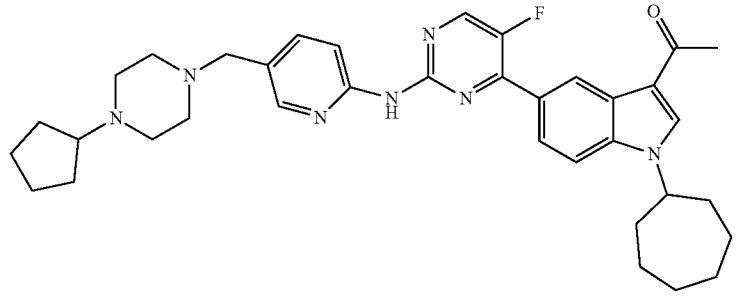 [SMILES: CC(=O)c1cn(C2CCCCCC2)c2ccc(-c3nc(Nc4ccc(CN5CCN(C6CCCC6)CC5)cn4)ncc3F)cc12] |
| I-21 | 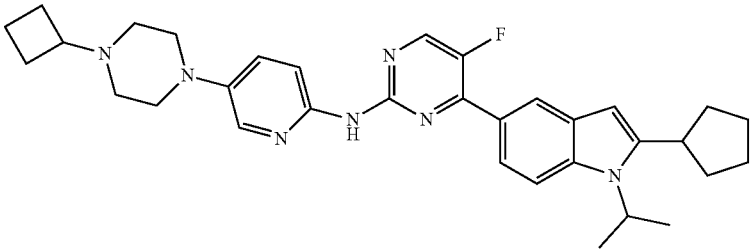 [SMILES: CC(C)n1c(C2CCCC2)cc2cc(-c3nc(Nc4ccc(N5CCN(C6CCC6)CC5)cn4)ncc3F)ccc21] |
| I-22 | 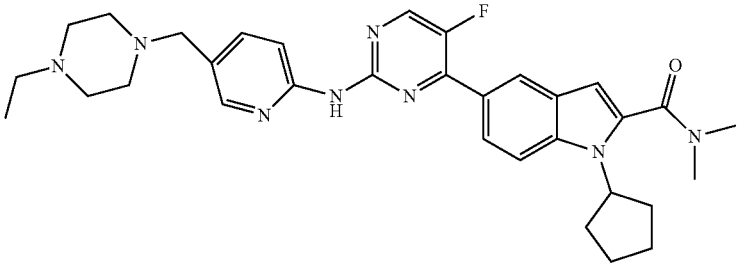 [SMILES: CCN1CCN(Cc2ccc(Nc3ncc(F)c(-c4ccc5c(c4)cc(C(=O)N(C)C)n5C4CCCC4)n3)nc2)CC1] |
| I-23 | 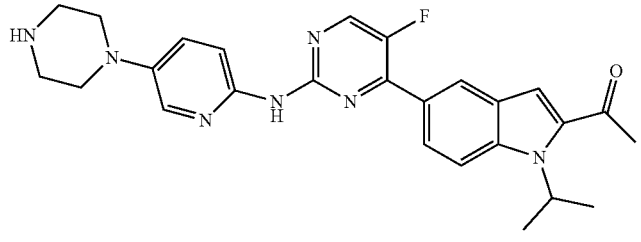 [SMILES: CC(=O)c1cc2cc(-c3nc(Nc4ccc(N5CCNCC5)cn4)ncc3F)ccc2n1C(C)C] |
| I-24 | 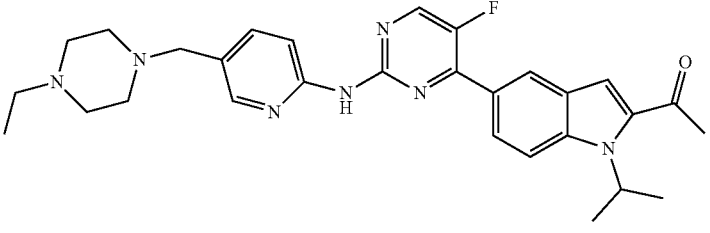 [SMILES: CCN1CCN(Cc2ccc(Nc3ncc(F)c(-c4ccc5c(c4)cc(C(C)=O)n5C(C)C)n3)nc2)CC1] |
| I-25 | 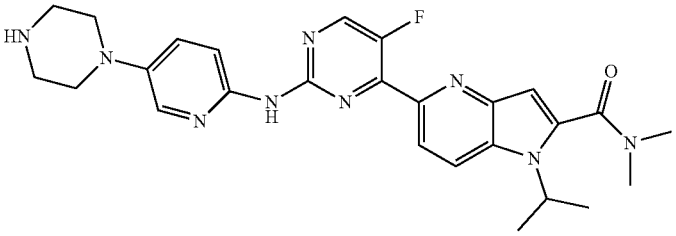 [SMILES: CC(C)n1c(C(=O)N(C)C)cc2nc(-c3nc(Nc4ccc(N5CCNCC5)cn4)ncc3F)ccc21] |

TABLE 1-continued

| Compound | Structure |
|---|---|
| I-26 | 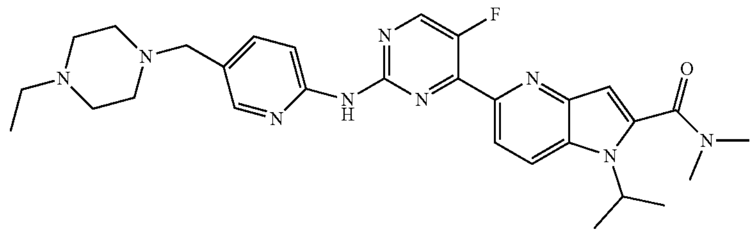 [SMILES: CCN1CCN(Cc2ccc(Nc3ncc(F)c(-c4ccc5c(cc(C(=O)N(C)C)n5C(C)C)n4)n3)nc2)CC1] |
| I-27 | 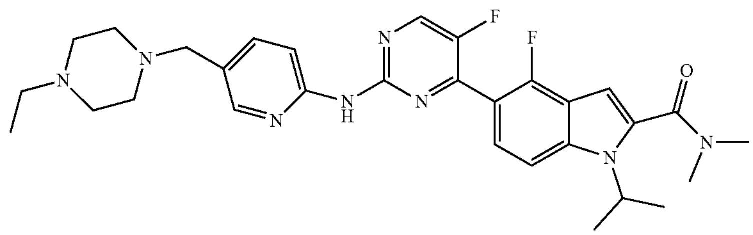 [SMILES: CCN1CCN(Cc2ccc(Nc3ncc(F)c(-c4ccc5c(cc(C(=O)N(C)C)n5C(C)C)c4F)n3)nc2)CC1] |
| I-28 | 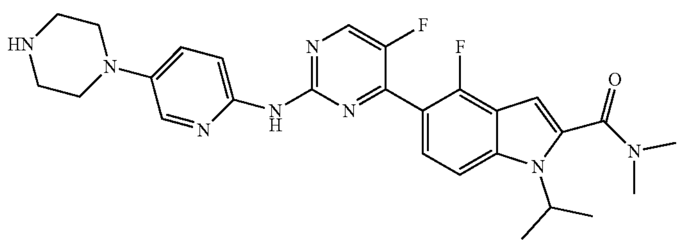 [SMILES: CC(C)n1c(C(=O)N(C)C)cc2c(F)c(-c3nc(Nc4ccc(N5CCNCC5)cn4)ncc3F)ccc21] |
| I-29 | 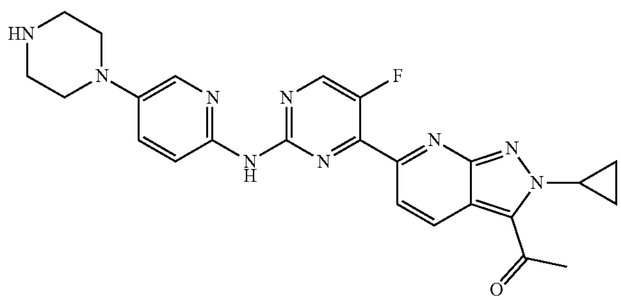 [SMILES: CC(=O)c1c2ccc(-c3nc(Nc4ccc(N5CCNCC5)cn4)ncc3F)nc2nn1C1CC1] |
| I-30 | 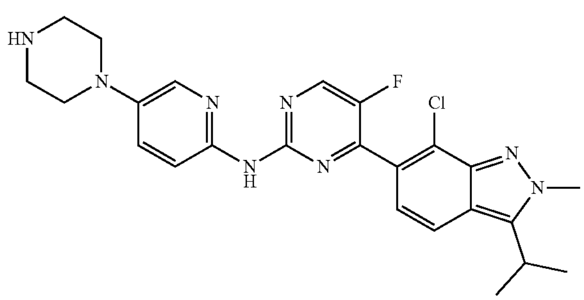 [SMILES: CC(C)c1c2ccc(-c3nc(Nc4ccc(N5CCNCC5)cn4)ncc3F)c(Cl)c2nn1C] |

TABLE 1-continued
| Compound | Structure |
|---|---|
| I-31 | 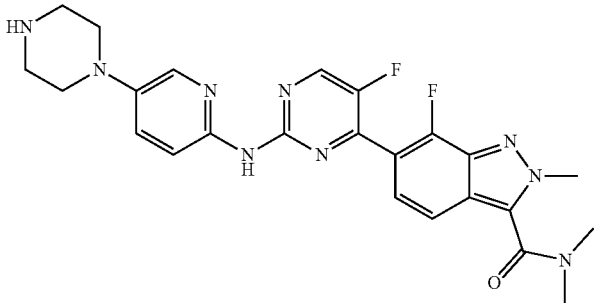 [SMILES: CN(C)C(=O)c1c2ccc(-c3nc(Nc4ccc(N5CCNCC5)cn4)ncc3F)c(F)c2nn1C] |
| I-32 | 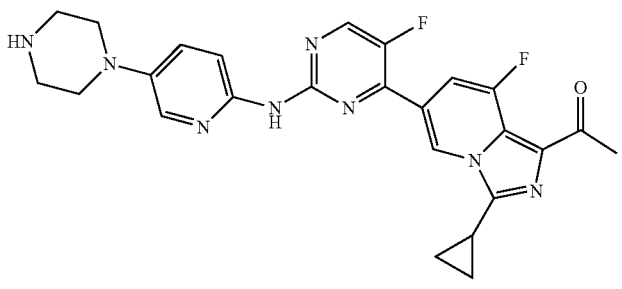 [SMILES: CC(=O)c1nc(C2CC2)n2cc(-c3nc(Nc4ccc(N5CCNCC5)cn4)ncc3F)cc(F)c12] |
| I-33 | 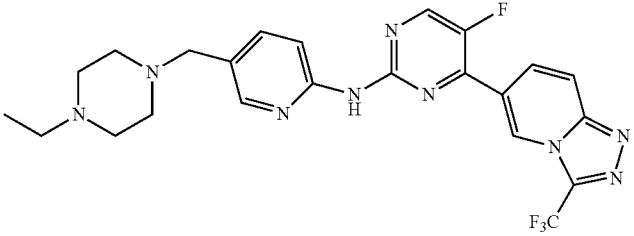 [SMILES: CCN1CCN(Cc2ccc(Nc3ncc(F)c(-c4ccc5nnc(C(F)(F)F)n5c4)n3)nc2)CC1] |
| I-34 | 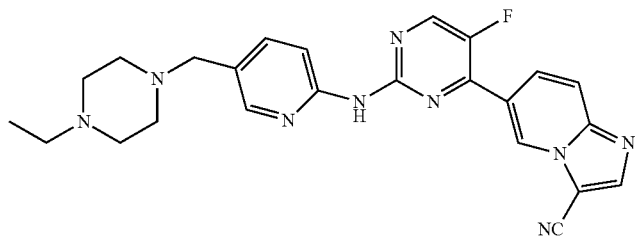 [SMILES: CCN1CCN(Cc2ccc(Nc3ncc(F)c(-c4ccc5ncc(C#N)n5c4)n3)nc2)CC1] |
| I-35 | 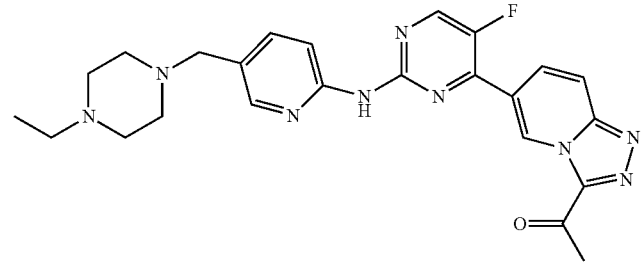 [SMILES: CCN1CCN(Cc2ccc(Nc3ncc(F)c(-c4ccc5nnc(C(C)=O)n5c4)n3)nc2)CC1] |

TABLE 1-continued
| Compound | Structure |
| --- | --- |
| I-36 | 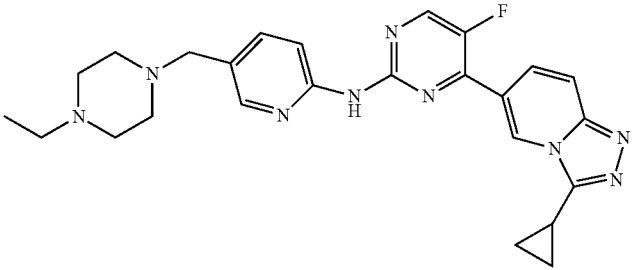 [SMILES: CCN1CCN(Cc2ccc(Nc3ncc(F)c(-c4ccc5nnc(C6CC6)n5c4)n3)nc2)CC1] |
| I-37 | 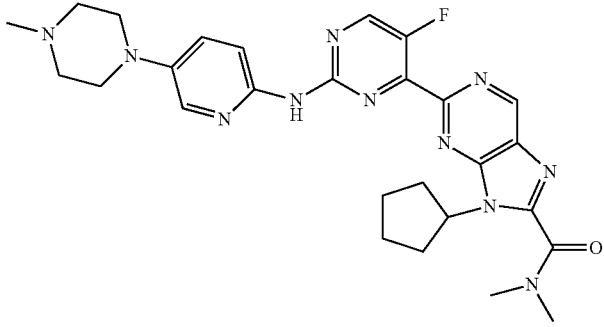 [SMILES: CN1CCN(c2ccc(Nc3ncc(F)c(-c4ncc5nc(C(=O)N(C)C)n(C6CCCC6)c5n4)n3)nc2)CC1] |
| I-38 | 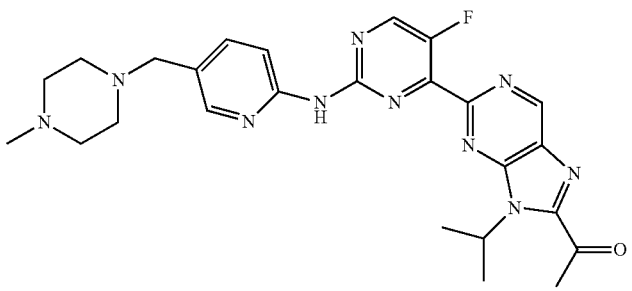 [SMILES: CC(=O)c1nc2cnc(-c3nc(Nc4ccc(CN5CCN(C)CC5)cn4)ncc3F)nc2n1C(C)C] |
| I-39 | 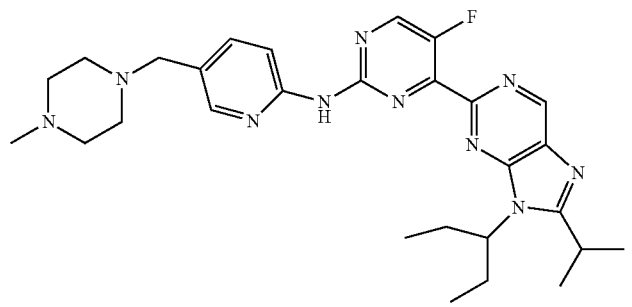 [SMILES: CCC(CC)n1c(C(C)C)nc2cnc(-c3nc(Nc4ccc(CN5CCN(C)CC5)cn4)ncc3F)nc21] |
| I-40 | 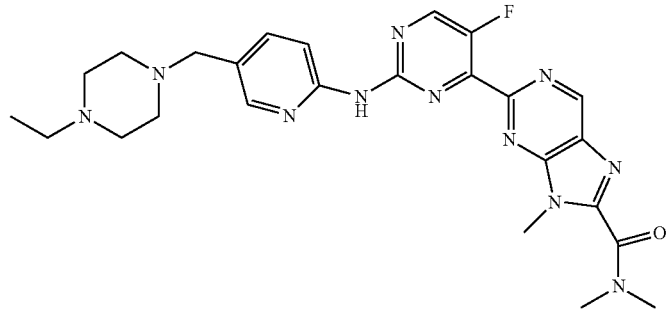 [SMILES: CCN1CCN(Cc2ccc(Nc3ncc(F)c(-c4ncc5nc(C(=O)N(C)C)n(C)c5n4)n3)nc2)CC1] |

TABLE 1-continued

| Compound | Structure |
|---|---|
| I-41 | 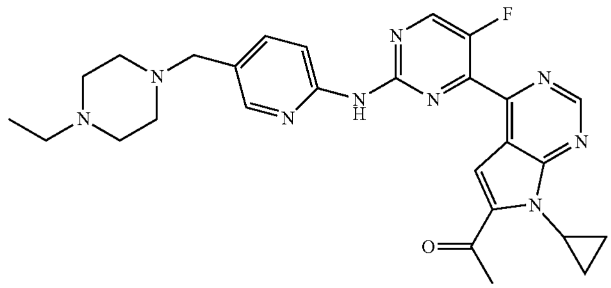 [SMILES: CCN1CCN(Cc2ccc(Nc3ncc(F)c(-c4ncnc5c4cc(C(C)=O)n5C4CC4)n3)nc2)CC1] |
| I-42 | 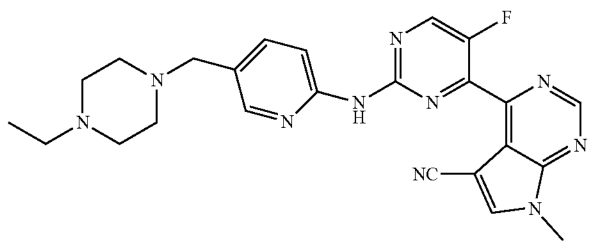 [SMILES: CCN1CCN(Cc2ccc(Nc3ncc(F)c(-c4ncnc5c4c(C#N)cn5C)n3)nc2)CC1] |
| I-43 | 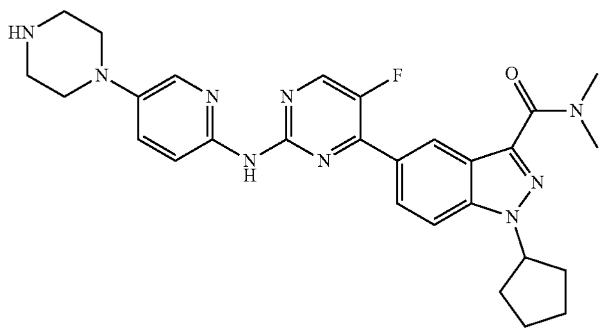 [SMILES: CN(C)C(=O)c1nn(C2CCCC2)c2ccc(-c3nc(Nc4ccc(N5CCNCC5)cn4)ncc3F)cc12] |
| I-44 | 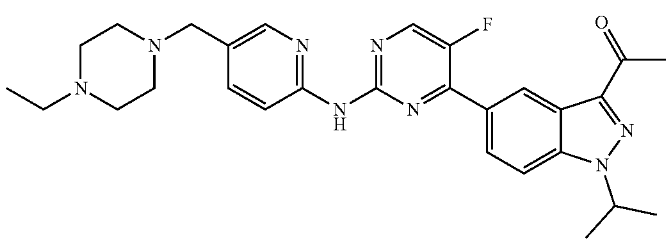 [SMILES: CCN1CCN(Cc2ccc(Nc3ncc(F)c(-c4ccc5c(c4)c(C(C)=O)nn5C(C)C)n3)nc2)CC1] |
| I-45 | 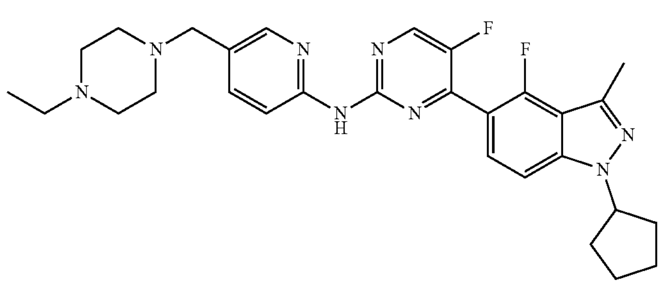 [SMILES: CCN1CCN(Cc2ccc(Nc3ncc(F)c(-c4ccc5c(c(C)nn5C5CCCC5)c4F)n3)nc2)CC1] |

TABLE 1-continued

| Compound | Structure |
|---|---|
| I-46 | 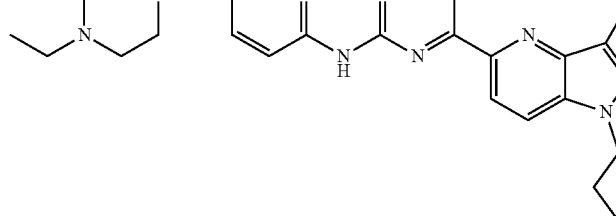 |
| I-47 | 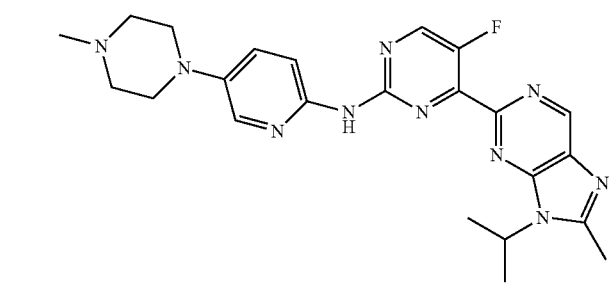 |
| I-48 | 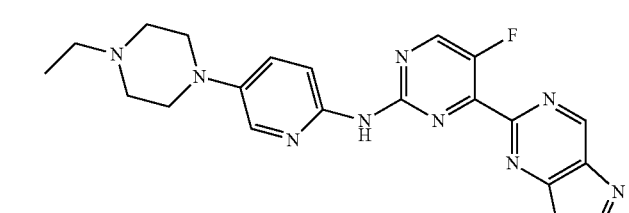 | or a pharmaceutically acceptable salt thereof.

Examples of a pharmaceutically acceptable salt include inorganic and organic salts such as hydrochloride, hydrobromide, sulfate, phosphate, citrate, tartrate, succinate, maleate, fumarate, mandelate and oxalate.

The compound of the present disclosure can be prepared by the following synthetic scheme 1:

The final product I is prepared according to the procedure reported in the literature (COATES DAVID ANDREW et al. WO2010075074A1), i.e., the substituted 2-chloropyrimidine ($I_1$) and the amine ($I_2$) are subjected to a catalytic reaction to give the target product I.

The preparation of 2-chloropyrimidine ($I_1$) can be prepared according to the following scheme 2 and 3.

Scheme 2:

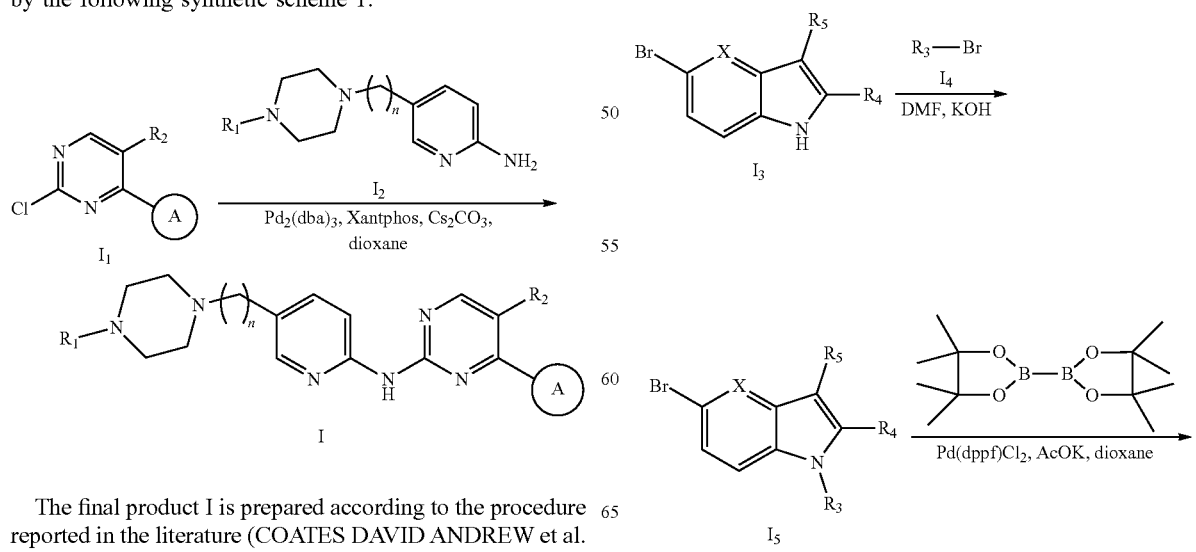

-continued

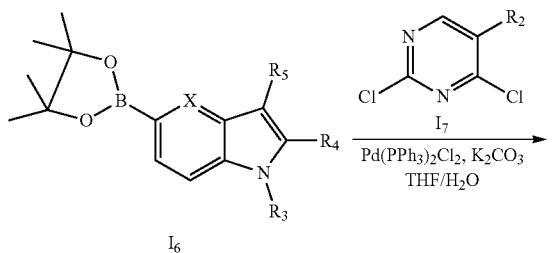

I₆

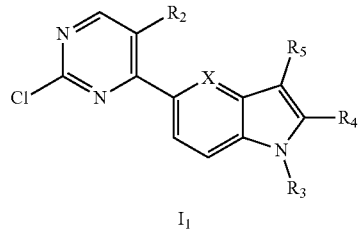

I₁

According to the method in references (B Corbel, F O Michaud et al. J. Heter. Chem. 2007, pp 793 and M O Frederick, D P Kjell, Tetra. Lett. 2015, pp 949), a starting material I₃ is reacted with bromide (I₄) under alkaline conditions to obtain I₅ which is subjected to Suzuki coupling reaction with bis-boronic acid pinacol ester and 2,4-dichloropyrimidine (I₇), respectively to obtain The following I₁ compounds can also be prepared according to scheme 2:

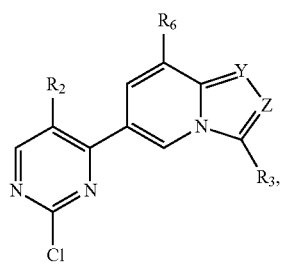

I₁

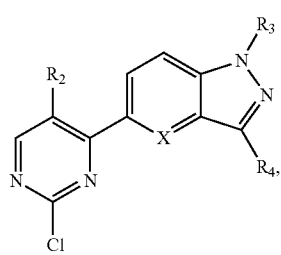

I₁

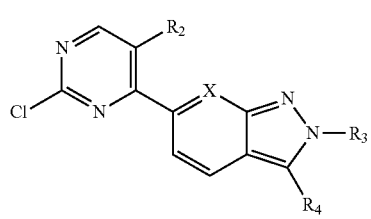

Scheme 2:

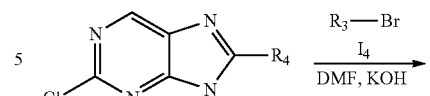

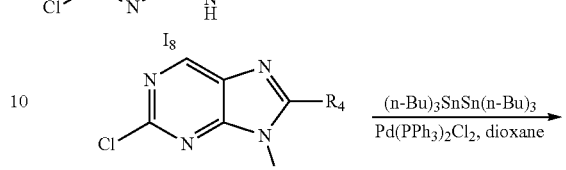

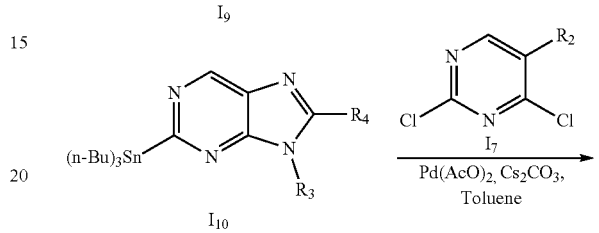

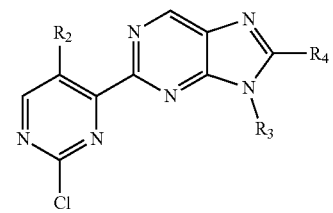

I₁

According to the method in references (A J Majeed, Ø Antonsen, et al. Tetra. 1989, pp 993; GattiMcarthur, Silvia, Goetschi, Erwin et al. WO2007110337A1 and Chen, Yuzhong; Sharpe, et al. WO2009061761A2), a starting material I₈ is reacted with bromide (I₄) under alkaline conditions to obtain I₉ which is coupled with hexabutyldistannane and 2,4-dichloropyrimidine (I₇), respectively to obtain I₁.

The following I₁ compounds can also be prepared according to scheme 3:

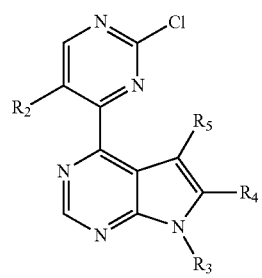

I₁

The present disclosure relates to said 2,4-disubstituted pyrimidine derivatives as CDK4/6 inhibitors that can be used for various clinical diseases caused by dysregulation of the cell cycle wherein CDK4/6 involves, such as cancer. Such diseases include but not limited to breast cancer, ovarian cancer, prostate cancer, colorectal cancer, liver cancer, melanoma, acute lymphocytic leukemia, chronic lymphocytic leukemia, multiple myeloma, lung cancer, gastric cancer, pancreatic cancer.

In the treatment of the disease, the derivative of the present disclosure can be used in composition to treat related cancers and other diseases by oral, injection or the like.

The composition comprises a therapeutically effective amount of a compound as described above or a pharmaceutically acceptable salt thereof and a pharmaceutically acceptable carrier.

The carrier refers to a conventional carrier in the pharmaceutical field, such as a diluent, an excipient such as water, a binder such as a cellulose derivative, gelatin, polyvinylpyrrolidone, etc.; a filler such as starch, etc.; a cracking agent such as calcium carbonate, sodium bicarbonate. Additionally, other adjuvants such as flavoring agents and sweeteners may also be added to the composition.

When used orally, they can be prepared into conventional solid preparations such as tablets, powders or capsules, etc.; when used for injection, they can be prepared as injections.

Various dosage forms of the composition of the present disclosure can be prepared with a conventional method in the medical field, wherein the content of the active ingredient is from 0.1% to 99.5% by weight.

The administration amount of the present disclosure can be varied according to the route of administration, the age, body weight of the patient, and the type and severity of the disease to be treated, and the daily dose thereof is 0.005-30 mg/kg body weight (for oral) or 0.005-30 mg/kg body weight (for injection).

The Advantageous Effect

The present disclosure provides a novel 2,4-disubstituted pyrimidine derivative or a pharmaceutically acceptable salt thereof and a use of the compound as a novel CDK4/6 inhibitor in the preparation of a medicament for the prevention or treatment of CDK4/6-related diseases. The various diseases caused by the imbalance of the cycle control involved with CDK4/6, especially malignant tumors to be treated include, but are not limited to breast cancer, ovarian cancer, prostate cancer, colorectal cancer, pancreatic cancer, liver cancer, melanoma, gastric cancer, and solid tumors and the like.

DETAILED DESCRIPTION

Embodiments of the Present Disclosure

Embodiment 1

Compound (I-1)

N-(5-(4-ethylpiperazine-1-methyl)-pyridin-2-yl)-5-fluoro-4-(1-isopropyl-1H-indol-5-yl)-pyrimidin-2-amine Step 1: 5-bromoindole (1.0 g, 5.1 mmol), 2-bromopropane (0.94 g, 7.65 mmol), and potassium hydroxide (0.43 g, 7.65 mmol) were added to N,N-dimethylformamide (DMF) (10 mL), and the reaction was carried out at 70° C. under $N_2$ protection for 10 h. The reaction mixture was stirred and extracted with $H_2O$ (50 mL)/ethyl acetate (50 mL). The organic layer was dried, filtered, concentrated and subjected to a silica gel column (eluent: ethyl acetate/petroleum ether: 1/30-1/10) to give 1-isopropyl-5-bromo-1H-indole (0.8 g, yield 66%) as a white solid.

Step 2: 1-isopropyl-5-bromo-1H-indole (0.8 g, 3.36 mmol), bis-boronic acid pinacol ester (1.02 g, 4.0 mmol), Pd(dppf)Cl$_2$ (0.25 g, 0.34 mmol), potassium acetate (0.66 g, 6.72 mmol) was added to 1,4-dioxane (15 mL), and the reaction was carried out at 80° C. under $N_2$ protection for 5 h. The solvent was concentrated to dry, the residue was stirred and extracted with $H_2O$ (50 mL)/ethyl acetate (50 mL), and the organic layer was dried, filtered and concentrated to give crude 1-isopropyl-5-boronic acid pinacol ester-1H-indole (0.96 g, calculated as 100% yield).

Step 3: 1-isopropyl-5-boronic acid pinacol ester-1H-indole (0.96 g, 3.36 mmol), 2,4-dichloro-5-fluoropyrimidine (0.62 g, 3.7 mmol), Pd(PPh$_3$)$_2$Cl$_2$ (0.23 g, 0.34 mmol) and K$_2$CO$_3$ (0.93 g, 8.66 mmol) were added into tetrahydrofuran (15 mL)/H$_2$O (3 mL) and the reaction was carried out at 80° C. under $N_2$ protection for 6 h. The reaction mixture was stirred and extracted with $H_2O$ (50 mL)/ethyl acetate (50 mL). The organic layer was dried, filtered, concentrated and subjected to a silica gel column (eluent: ethyl acetate/petroleum ether: 1/30-1/20) to give 1-isopropyl-5-(2-chloro-5-fluoropyrimidin-4-yl)-1H-indole (0.5 g, yield of 51.5% over two steps) as a white solid, MS(m/z): 291 [M+H]$^+$.

Step 4: 1-isopropyl-5-(2-chloro-5-fluoropyrimidin-4-yl)-1H-indole (150 mg, 0.52 mmol), 5-[(4-ethylpiperazine-1-yl)-methyl]-pyridin-2-amine (114 mg, 0.52 mmol), Pd$_2$(dba)$_3$ (50 mg, 0.052 mmol), Xantphos (45 mg, 0.05278 mmol) and cesium carbonate (254 mg, 0.78 mmol) were added into 1,4-dioxane (815 mL) and the reaction was carried out at 100° C. under $N_2$ protection for 8 h. The solvent was concentrated to dry and the residue was stirred and extracted with $H_2O$ 30 mL)/dichloromethane (DCM, 50 mL). The organic layer was dried, filtered, and concentrated to give a pale yellow solid. The residue was purified on a silica gel column (eluent: dichloromethane/methanol: 1/30-1/20) to give N-(5-(4-ethylpiperazine-1-methyl)-pyridin-2-yl)-5-fluoro-4-(1-isopropyl-1H-indol-5-yl)pyrimidin-2-amine (I-1, 125 mg, yield 50.9%) as a pale yellow solid, MS(m/z): 474 [M+H]$^+$. $^1$H NMR (DMSO-d$_6$): δ: 11.91 (br, 1H), 11.62 (br, 1H), 8.78-8.77 (d, J=4.0 Hz, 1H), 8.60 (s, 1H), 8.41 (s, 1H), 8.38-8.36 (d, J=8.0 Hz, 1H), 8.03-8.01 (d, J=8.0 Hz, 1H), 7.97-7.95 (d, J=8.0 Hz, 1H), 7.76-7.74 (d, J=8.0 Hz, 1H), 7.67-7.66 (d, J=4.0 Hz, 1H), 6.69-6.68 (d, J=4.0 Hz, 1H), 4.89-4.82 (m, 1H), 4.42 (m, 6H), 3.17 (m, 4H), 1.50-1.49 (d, J=4.0 Hz, 6H), 1.28-1.24 (t, J=8.0 Hz, 3H).

Embodiment 2

Compound (I-2)

N-(5-(piperazin-1-yl)-pyridin-2-yl)-5-fluoro-4-(1-isopropyl-1H-indol-5-yl)pyrimidine 2-amine Compound I-2 was synthesized according to the method in Embodiment 1. The starting materials were 1-isopropyl-5-(2-chloro-5-fluoropyrimidin-4-yl)-1H-indole and 4-(6-aminopyridin-3-yl)piperazine-1-tert-butyl carboxylate. N-(5-(4-tert-butyl carboxylate-1-piperazinyl)-pyridine-2-yl)-5-fluoro-4-(1-isopropyl-1H-indol-5-yl)pyrimidin-2-amine was obtained by Step 4 in Embodiment 1, and such intermediate was subjected to deprotection of BOC with 3N ethyl acetate hydrochloride to give a pale yellow solid title product of N-(5-(piperazin-1-yl)-pyridin-2-yl)-5-fluoro-4-(1-isopropyl-1H-indol-5-yl)pyrimidin-2-amine hydrochloride (I-2). MS(m/z): 432 [M+H]$^+$. $^1$H NMR (DMSO-d$_6$): δ: 11.65 (br, 1H), 9.70 (br, 2H), 8.77-8.76 (d, J=4.0 Hz, 1H), 8.39 (s, 1H), 8.01-8.00 (d, J=4.0 Hz, 1H), 7.96 (s, 1H), 7.93 (s, 1H), 7.85-7.83 (d, J=8.0 Hz, 1H), 7.76-7.74 (d, J=8.0 Hz, 1H), 7.68-7.67 (d, J=4.0 Hz, 1H), 6.69-6.68 (d, J=4.0 Hz, 1H), 4.89-4.82 (m, 1H), 3.69-3.46 (m, 8H), 1.51-1.49 (d, J=8.0 Hz, 6H).

Embodiment 3

Compound (I-3)

N-(5-(piperazin-1-yl)-pyridin-2-yl)-5-fluoro-4-(1-cyclopentyl-3-acetyl-1H-indol-5-yl)pyrimidin-2-amine Compound I-3 was synthesized according to the method in Embodiment 1. The starting materials were 1-cyclopentyl-3-acetyl-5-(2-chloro-5-fluoropyrimidin-4-yl)-1H-indole (the synthesis method was similar to that in Embodiment 1, and the starting materials were 2,4-dichloro-5-fluoropyrimidine and 1-cyclopentyl-3-acetyl-5-boronic acid pinacol ester-1H-indole (starting materials were bromocyclopentane and 3-acetyl-5-bromo-1H-indole)) and 4-(6-aminopyridin-3-yl)piperazine-1-tert-butyl carboxylate. The title product of N-(5-(piperazin-1-yl)-pyridin-2-yl)-5-fluoro-4-(1-cyclopentyl-3-acetyl-1H-indol-5-yl)pyrimidin-2-amine hydrochloride (I-3) was obtained as a pale yellow solid. MS(m/z): 500 [M+H]$^+$. $^1$H NMR (DMSO-d$_6$): δ: 11.67 (br, 1H), 9.73 (br, 2H), 9.39 (s, 1H), 8.78 (s, 1H), 8.69-8.67 (d, J=8.0 Hz, 1H), 8.00-7.97 (m, 2H), 7.93 (s, 1H), 7.72-7.69 (m, 2H), 4.89-4.83 (m, 1H), 3.69-3.46 (m, 8H), 2.73 (s, 3H), 2.02-1.67 (m, 8H).

Embodiment 4

Compound (I-4)

N-(5-(4-ethylpiperazine-1-methyl)-pyridin-2-yl)-5-fluoro-4-(1-cyclopentyl-3-acetyl-1H-indol-5-yl)pyrimidin-2-amine Compound I-4 was synthesized according to the method in Embodiment 1. The starting materials were 1-cyclopentyl-3-acetyl-5-(2-chloro-5-fluoropyrimidin-4-yl)-1H-indole and 5-[(4-ethylpiperazin-1-yl)methyl]pyridin-2-amine. The title product of N-(5-(4-ethylpiperazin-1-methyl)-pyridin-2-yl)-5-fluoro-4-(1-cyclopentyl-3-acetyl-1H-indol-5-yl)pyrimidin-2-amine (I-4) was obtained as a pale yellow solid. MS(m/z): 542[M+H]$^+$. $^1$H NMR (DMSO-d$_6$): δ: 11.93 (br, 1H), 11.63 (br, 1H), 9.39 (s, 1H), 8.78-8.77 (d, J=4.0 Hz, 1H), 8.61 (s, 1H), 8.41 (s, 1H), 8.39-8.36 (m, 2H), 7.97-7.95 (d, J=8.0 Hz, 1H), 7.67-7.65 (d, J=8.0 Hz, 1H), 4.89-4.82 (m, 1H), 4.57 (s, 2H), 4.41-4.21 (m, 13H), 2.01-1.69 (m, 8H), 1.28-1.24 (t, J=8.0 Hz, 3H).

Embodiment 5

Compound (I-5)

N-(5-(piperazin-1-yl)-pyridin-2-yl)-5-fluoro-4-(2,3-dimethyl-2H-indazol-6-yl)pyrimidin-2-amine Compound I-5 was synthesized according to the method in Embodiment 1, and the starting materials were 2,3-dimethyl-6-(2-chloro-5-fluoropyrimidin-4-yl)-2H-indazole (its synthesis method was similar to that in Embodiment 1, and the starting materials were 2,4-dichloro-5-fluoropyrimidine and 2,3-dimethyl-6-bromo-2H-indazole) and 4-(6-aminopyridin-3-yl)piperazine-1-tert-butyl carboxylate. The title product of N-(5-(piperazin-1-yl)-pyridin-2-yl)-5-fluoro-4-(2,3-dimethyl-2H-indazol-6-yl)pyrimidin-2-amine hydrochloride (I-5) was obtained as a pale yellow solid. MS(m/z): 419 [M+H]$^+$. $^1$H NMR (DMSO-d$_6$): δ: 11.68 (br, 1H), 9.75 (br, 2H), 9.37 (s, 1H), 8.80-8.78 (d, J=8.0 Hz, 1H), 8.75 (s, 1H), 8.00-7.97 (m, 2H), 7.72-7.69 (m, 2H), 4.53 (s, 3H), 4.35-4.21 (m, 11H).

Embodiment 6

Compound (I-6)

N-(5-(4-ethylpiperazine-1-methyl)-pyridin-2-yl)-5-fluoro-4-(3-isopropyl-[1,2,4]triazolo[4,3-a]pyridin-6-yl)pyrimidin-2-amine Compound I-6 was synthesized according to the method in Embodiment 1, and the starting materials were 3-isopropyl-6-(2-chloro-5-fluoropyrimidin-4-yl)-[1,2,4]triazolo[4,3-a]pyridine (its synthesis method was similar to that in Embodiment 1, and the starting materials were 2,4-dichloro-5-fluoropyrimidine and 3-isopropyl-6-bromo-[1,2,4]triazolo[4,3-a]pyridine) and 5-[(4-ethylpiperazin-1-yl)methyl]pyridin-2-amine. The title product of N-(5-(4-ethylpiperazine-1-methyl)-pyridin-2-yl)-5-fluoro-4-(3-isopropyl-[1,2,4]triazolo[4,3-a]pyridin-6-yl)pyrimidin-2-amine (I-6) was obtained as a pale yellow solid. MS(m/z): 476[M+H]$^+$. $^1$H NMR (DMSO-d$_6$): δ: 11.93 (br, 1H), 11.61 (br, 1H), 9.67 (s, 1H), 9.37 (s, 1H), 8.83-8.79 (m, 2H), 8.51 (s, 1H), 7.79-7.77 (d, J=8.0 Hz, 1H), 7.03-7.01 (d, J=8.0 Hz, 1H), 4.88-4.83 (m, 1H), 4.57 (s, 2H), 4.21-4.02 (m, 9H), 1.53-1.51 (d, J=8.0 Hz, 6H), 1.28-1.24 (t, J=8.0 Hz, 3H).

Embodiment 7

Compound (I-7)

N-(5-(piperazin-1-yl)-pyridin-2-yl)-5-fluoro-4-(3-isopropyl-[1,2,4]triazolo[4,3-a]pyridine-6-yl)pyrimidin-2-amine Compound I-7 was synthesized according to the method in Embodiment 1, and the starting materials were 3-isopropyl-6-(2-chloro-5-fluoropyrimidin-4-yl)-[1,2,4]triazolo[4,3-a]pyridine and 4-(6-aminopyridin-3-yl)piperazine-1-tert-butyl carboxylate. The title product of N-(5-(piperazin-1-yl)-pyridin-2-yl)-5-fluoro-4-(3-isopropyl-[1,2,4]triazolo[4,3-a]pyridine-6-yl)pyrimidin-2-amine hydrochloride (I-7) was obtained as a pale yellow solid. MS(m/z): 434[M+H]$^+$. $^1$H NMR (DMSO-d$_6$): δ: 11.69 (br, 1H), 9.81 (br, 2H), 9.67 (s, 1H), 9.38 (s, 1H), 8.82-8.78 (m, 2H), 8.48 (s, 1H), 7.79-7.75 (m, 2H), 4.33-4.20 (m, 9H), 1.51-1.49 (d, J=8.0 Hz, 6H).

Embodiment 8

Compound (I-8)

N-(5-(piperazin-1-yl)-pyridin-2-yl)-5-fluoro-4-(9-isopropyl-8-methyl-9H-purin-2-yl)pyrimidin-2-amine 2-chloro-9-isopropyl-8-methyl-9H-purine (synthesis was performed according to Step 1 in Embodiment 1, 500 mg, 2.38 mmol), Pd(PPh$_3$)$_2$Cl$_2$ (167 mg, 0.24 mmol), hexabutyldistannane (1.45 g, 2.50 mmol) were added into 1,4-dioxane (10 mL) and reacted at 80° C. under N$_2$ protection for 5 h. The solvent was concentrated to dry and the residue was purified on a silica gel column (eluent: ethyl acetate/ petroleum ether: 1/30-1/20) to give 2-tri-n-butyltin-9-isopropyl-8-methyl-9H-purine (700 mg, yield 63.2%).

2-tri-n-butyltin-9-isopropyl-8-methyl-9H-purine (700 mg, 1.51 mmol), 2,4-dichloro-5-fluoropyrimidine (276 mg, 1.65 mmol), Pd(PPh$_3$)$_2$Cl$_2$ (110 mg, 0.15 mmol), K$_2$CO$_3$ (415 mg, 3.01 mmol) were added into 1,4-dioxane (10 mL) and the reaction was carried out at 80° C. under N$_2$ protection for 6 h. The reaction mixture was stirred and extracted with H$_2$O (50 mL)/ethyl acetate (50 mL). The organic layer was dried, filtered, concentrated and purified on a silica gel column (eluent: ethyl acetate/petroleum ether: 1/30-1/20) to give a white solid 9-isopropyl-8-methyl-2-(2-chloro-5-fluoropyrimidin-4-yl)-9H-purine (350 mg, yield 76.1%), MS(m/z): 308 [M+H]$^+$.

Compound I-8 was prepared according to the methods in Embodiments 1 and 2, 9-isopropyl-8-methyl-2-(2-chloro-5-fluoropyrimidin-4-yl)-9H-purine and 4-(6-aminopyridin-3-yl)piperazine-1-tert-butyl carboxylate were used as starting materials to give a pale yellow solid title product of N-(5-(piperazin-1-yl)-pyridin-2-yl)-5-fluoro-4-(9-isopropyl-8-methyl-9H-purin-2-yl)pyrimidin-2-amine hydrochloride (I-8). MS(m/z): 449[M+H]$^+$. $^1$H NMR (DMSO-d$_6$): δ: 11.68 (br, 1H), 9.83 (br, 2H), 9.81 (s, 1H), 9.39 (s, 1H), 8.85 (s, 1H), 8.02-8.00 (d, J=8.0 Hz, 1H), 7.93-7.91 (d, J=8.0 Hz, 1H), 5.86-5.81 (m, 1H), 4.32-4.20 (m, 8H), 2.85 (s, 3H), 1.55-1.54 (d, J=4.0 Hz, 6H).

Embodiment 9

Compound (I-9)

N-(5-(4-ethylpiperazine-1-methyl)-pyridin-2-yl)-5-fluoro-4-(9-isopropyl-8-methyl-9H-purin-2-yl)pyrimidin-2-amine Compound I-9 was synthesized according to the method in Embodiment 1, and the starting materials were 9-isopropyl-8-methyl-2-(2-chloro-5-fluoropyrimidin-4-yl)-9H-purine and 5-[(4-ethylpiperazin-1-yl)methyl]pyridin-2-amine. The title product of N-(5-(4-ethylpiperazin-1-methyl)-pyridin-2-yl)-5-fluoro-4-(9-isopropyl-8-methyl-9H-purin-2-yl)pyrimidin-2-amine (I-9) was obtained as a pale yellow solid. MS(m/z): 491 [M+H]$^+$. $^1$H NMR (DMSO-d$_6$): δ: 11.95 (br, 1H), 11.64 (br, 1H), 9.82 (s, 1H), 9.38 (s, 1H), 8.84 (s, 1H), 8.05-8.03 (d, J=8.0 Hz, 1H), 7.03-7.01 (d, J=8.0 Hz, 1H), 5.88-5.83 (m, 1H), 4.58 (s, 2H), 4.21-4.02 (m, 13H), 1.54-1.53 (d, J=4.0 Hz, 6H), 1.28-1.24 (t, J=8.0 Hz, 3H).

Embodiment 10

Compound (I-10) N-(5-(piperazin-1-yl)-pyridin-2-yl)-5-fluoro-4-(5-fluoro-6-formic acid diformamido-7-isopropyl-7H-pyrrolo[2,3-d]pyrimidin-4-yl)pyrimidin-2-amine Compound I-10 was synthesized according to the method in Embodiment 1, and the starting materials were 5-fluoro-6-formic acid diformamido-7-isopropyl-4-(2-chloro-5-fluoropyrimidin-4-yl)-7H-pyrrolo[2,3-d]pyrimidine (its synthesis was similar to that in Embodiment 8, the starting materials were 2,4-dichloro-5-fluoropyrimidine and 2-chloro-5-fluoro-6-formic acid diformamido-7-isopropyl-7H-pyrrolo[2,3-d]pyrimidine) and 4-(6-aminopyridin-3-yl)piperazine-1-tert-butyl carboxylate. The title product of N-(5-(piperazin-1-yl)-pyridin-2-yl)-5-fluoro-4-(5-fluoro-6-formic acid diformamido-7-isopropyl-7H-pyrrolo[2,3-d]pyrimidin-4-yl)pyrimidin-2-amine hydrochloride (I-10) was obtained as a pale yellow solid. MS(m/z): 523[M+H]$^+$. $^1$H NMR (DMSO-d$_6$): δ: 11.67 (br, 1H), 9.82 (br, 2H), 9.83 (s, 1H), 9.37 (s, 1H), 8.83 (s, 1H), 8.02-8.00 (d, J=8.0 Hz, 1H), 7.94-7.92 (d, J=8.0 Hz, 1H), 5.85-5.82 (m, 1H), 4.32-4.20 (m, 14H), 1.56-1.55 (d, J=4.0 Hz, 6H).

Embodiment 11

Compound (I-11)

N-(5-(4-ethylpiperazine-1-methyl)-pyridin-2-yl)-5-fluoro-4-(6-methyl-7-cyclopentyl-7H-pyrrolo[2,3-d]pyrimidin-4-yl)pyrimidin-2-amine Compound I-11 was synthesized according to the method in Embodiment 1, and the starting materials were 6-methyl-7-cyclopentyl-4-(2-chloro-5-fluoropyrimidin-4-yl)-7H-pyrrolo[2,3-d]pyrimidine (its synthesis was similar to that in Embodiment 10, the starting materials were 2,4-dichloro-5-fluoropyrimidine and 6-methyl-7-cyclopentyl-4-bromo-7H-pyrrolo[2,3-d]pyrimidine) and 5-[(4-ethylpiperazin-1-yl)methyl]pyridin-2-amine. The title product of N-(5-(4-ethylpiperazine-1-methyl)-pyridin-2-yl)-5-fluoro-4-(6-methyl-7-cyclopentyl-7H-pyrrolo[2,3-d]pyrimidin-4-yl)pyrimidin-2-amine (I-11) was obtained as a pale yellow solid. MS(m/z): 516[M+H]$^+$. $^1$H NMR (DMSO-d$_6$): δ: 11.93 (br, 1H), 11.62 (br, 1H), 9.84 (s, 1H), 9.38 (s, 1H), 8.83 (s, 1H), 8.04-8.02 (d, J=8.0 Hz, 1H), 7.00-6.98 (d, J=8.0 Hz, 1H), 6.63 (s, 1H), 4.89-4.83 (m, 1H), 4.59 (s, 2H), 4.21-4.03 (m, 10H), 2.10-1.68 (m, 11H), 1.26-1.22 (t, J=8.0 Hz, 3H).

Embodiment 12

Compound (I-12)

N-(5-(piperazin-1-yl)-pyridin-2-yl)-5-fluoro-4-(2-methyl-3-cyclopentyl-2H-7-azaindazol-6-yl)pyrimidin-2-amine Compound I-12 was synthesized according to the method in Embodiment 1, and the starting materials were 2-methyl-3-cyclopentyl-6-(2-chloro-5-fluoropyrimidin-4-yl)-2H-7-azaindazole (its synthesis was similar to that in Embodiment 1, and the starting materials were 2,4-dichloro-5-fluoropyrimidine and 2-methyl-3-cyclopentyl-6-bromo-2H-indazole) and 4-(6-aminopyridin-3-yl)piperazine-1-tert-butyl carboxylate. The title product of N-(5-(piperazin-1-yl)-pyridin-2-yl)-5-fluoro-4-(2-methyl-3-cyclopentyl-2H-7-azaindazol-6-yl)pyrimidin-2-amine hydrochloride (I-12) was obtained as a pale yellow solid. MS(m/z): 474[M+H]$^+$. $^1$H NMR (DMSO-d$_6$): δ: 11.71 (br, 1H), 9.79 (br, 2H), 9.38 (s, 1H), 8.80-8.78 (d, J=8.0 Hz, 1H), 8.73 (s, 1H), 7.58 (s, 1H), 7.23-7.19 (m, 2H), 4.47 (s, 3H), 4.36-4.21 (m, 8H), 1.57-1.29 (m, 8H).

Embodiment 13

Compound (I-13)

N-(5-(piperazin-1-yl)-pyridin-2-yl)-5-fluoro-4-(1-isopropyl-3-formamido-4-fluoro-1H-indazol-5-yl)pyrimidin-2-amine Compound I-13 was synthesized according to the method in Embodiment 1, and the starting materials were 1-isopropyl-3-formamido-4-fluoro-5-(2-chloro-5-fluoropyrimidin-4-yl)-1H-indazole (its synthesis was similar to that in Embodiment 1, and the starting materials were 2,4-dichloro-5-fluoropyrimidine and 1-isopropyl-3-formamido-4-fluoro- 5-bromo-1H-indazole (the starting materials are bromoisopropane and 3-formamido-4-fluoro-5-bromo-1H-indazole)) and 4-(6-aminopyridin-3-yl)piperazine-1-tert-butyl carboxylate. The title product of N-(5-(piperazin-1-yl)-pyridin-2-yl)-5-fluoro-4-(1-isopropyl-3-formamido-4-fluoro-1H-indazol-5-yl)pyrimidin-2-amine hydrochloride (I-13) was obtained as a pale white solid. MS(m/z): 494[M+H]$^+$. $^1$H NMR (DMSO-d$_6$): δ: 12.11 (br, 2H), 11.68 (br, 1H), 9.71 (br, 2H), 9.39 (s, 1H), 8.68-8.66 (d, J=8.0 Hz, 1H), 8.02-8.00 (d, J=8.0 Hz, 1H), 7.95 (s, 1H), 7.73-7.69 (m, 2H), 4.87-4.82 (m, 1H), 3.67-3.46 (m, 8H), 1.24-1.20 (d, J=8.0 Hz, 6H).

Embodiment 14

Compound (I-14)

N-(5-(piperazin-1-yl)-pyridin-2-yl)-5-fluoro-4-(1-cyclopentyl-2-formic acid diformamido-1H-indol-5-yl)pyrimidin-2-amine Compound I-14 was synthesized according to the method in Embodiment 1, and the starting materials were 1-cyclopentyl-2-formic acid diformamido-5-(2-chloro-5-fluoropyrimidin-4-yl)-1H-indole (its synthesis was similar to that in Embodiment 1, and the starting materials were 2,4-dichloro-5-fluoropyrimidine and 1-cyclopentyl-2-formic acid diformamido-5-boronic acid pinacol ester-1H-indole (the starting materials were bromocyclopentane and 2-formic acid diformamido-5-bromo-1H-indole)) and 4-(6-aminopyridin-3-yl)piperazine-1-c tert-butyl arboxylate. The title product of N-(5-(piperazin-1-yl)-pyridin-2-yl)-5-fluoro-4-(1-cyclopentyl-2-formic acid diformamido-1H-indol-5-yl)pyrimidin-2-amine hydrochloride (I-14) was obtained as a pale white solid. MS(m/z): 529 [M+H]$^+$. $^1$H NMR (DMSO-d$_6$): δ: 11.66 (br, 1H), 9.71 (br, 2H), 9.38 (s, 1H), 8.78 (s, 1H), 8.67-8.65 (d, J=8.0 Hz, 1H), 8.01-7.97 (m, 2H), 7.95 (s, 1H), 7.71-7.69 (m, 2H), 4.88-4.82 (m, 1H), 3.68-3.46 (m, 14H), 2.01-1.68 (m, 8H).

Embodiment 15

Compound (I-15)

N-(5-(4-methylpiperazine-1-methyl)-pyridin-2-yl)-5-chloro-4-(1-(3-pentyl)-2-acetyl-1H-indol-5-yl)pyrimidin-2-amine Compound I-15 was synthesized according to the method in Embodiment 1, and the starting materials were 1-(3-pentyl)-2-acetyl-5-(2-chloro-5-fluoropyrimidin-4-yl)-1H-indole (its synthesis was similar to that in Embodiment 1, and the starting materials were 2,4-dichloro-5-fluoropyrimidine and 1-(3-pentyl)-2-acetyl-5-boronic acid pinacolester-1H-indole (the starting materials were 3-bromopentane and 2-acetyl-5-bromo-1H-indole)) and 5-[(4-methylpiperazin-1-yl)methyl]pyridine-2-amine. The title product of N-(5-(4-methylpiperazin-1-methyl)-pyridin-2-yl)-5-chloro-4-(1-(3-pentyl)-2-acetyl-1H-indol-5-yl)pyrimidin-2-amine (I-15) was obtained as a white solid. MS(m/z): 547 [M+H]$^+$. $^1$H NMR (DMSO-d$_6$): δ: 11.91 (br, 1H), 11.62 (br, 1H), 9.38 (s, 1H), 8.76-8.75 (d, J=4.0 Hz, 1H), 8.60 (s, 1H), 8.40 (s, 1H), 8.37-8.34 (m, 2H), 7.97-7.95 (d, J=8.0 Hz, 1H), 7.66-7.64 (d, J=8.0 Hz, 1H), 4.87-4.82 (m, 1H), 4.56 (s, 2H), 4.40-4.21 (m, 8H), 2.42 (s, 3H), 2.37 (s, 3H), 2.03-1.98 (m, 4H), 1.02-0.98 (m, 6H).

Embodiment 16

Compound (I-16)

N-(5-(4-isopropylpiperazin-1-methyl)-pyridin-2-yl)-4-(1,2-dimethyl-3-trifluoromethyl-1H-indol-5-yl)pyrimidin-2-amine Compound I-16 was synthesized according to the method in Embodiment 1, and the starting material were 1,2-dimethyl-3-trifluoromethyl-5-(2-chloro-pyrimidin-4-yl)-1H-indole (its synthesis was similar to that in Embodiment 1, and the starting materials were 2,4-dichloropyrimidine and 1,2-dimethyl-3-trifluoromethyl-5-boronic acid pinacol ester-1H-indole (the starting materials were methyl iodide and 2-methyl-3-trifluoromethyl-5-bromo-1H-indole)) and 5-[(4-isopropylpiperazin-1-yl)methyl]pyridine 2-amine. The title product of N-(5-(4-isopropylpiperazin-1-methyl)-pyridin-2-yl)-4-(1,2-dimethyl-3-trifluoromethyl-1H-indol-5-yl)pyrimidin-2-amine (I-16) was obtained as a white solid. MS(m/z): 524[M+H]$^+$. $^1$H NMR (DMSO-d$_6$): δ: 11.90 (br, 1H), 11.63 (br, 1H), 9.35 (s, 1H), 8.78-8.77 (d, J=4.0 Hz, 1H), 8.58 (s, 1H), 8.38-8.35 (m, 2H), 7.93-7.88 (m, 2H), 7.35 (s, 1H), 4.57 (s, 2H), 4.52 (s, 3H), 4.42-4.19 (m, 12H), 1.25-1.21 (d, J=8.0 Hz, 6H).

Embodiment 17

Compound (I-17)

N-(5-(4-cyclopropylpiperazine-1-methyl)-pyridin-2-yl)-5-fluoro-4-(1-cyclopropyl-2-cyano-3-isopropyl-1H-indol-5-yl)pyrimidin-2-amine Compound I-17 was synthesized according to the method in Embodiment 1, and the starting materials were 1-cyclopropyl-2-cyano-3-isopropyl-5-(2-chloro-pyrimidin-4-yl)-1H-indole (its synthesis was similar to that in Embodiment 1, and the starting materials were 2,4-dichloro-5-fluoropyrimidine and 1-cyclopropyl-2-cyano-3-isopropyl-5-boronic acid pinacol ester-1H-indole (the starting materials were bromocyclopropane and 1-cyclopropyl-2-cyano-5-bromo-1H-indole)) and 5-[(4-cyclopropylpiperazin-1-yl)methyl]pyridin-2-amine. The title product of N-(5-(4-cyclopropylpiperazine-1-methyl)-pyridin-2-yl)-5-fluoro-4-(1-cyclopropyl-2-cyano-3-isopropyl-1H-indol-5-yl)pyrimidin-2-amine (I-17) was obtained as a pale yellow solid. MS(m/z): 552[M+H]$^+$. $^1$H NMR (DMSO-d$_6$): δ: 11.91 (br, 1H), 11.62 (br, 1H), 9.33 (s, 1H), 8.78-8.75 (m, 2H), 8.39-8.36 (m, 2H), 7.91-7.88 (m, 1H), 7.37 (s, 1H), 4.56 (s, 2H), 4.43-4.19 (m, 10H), 1.25-1.20 (m, 7H), 0.95-0.82 (m, 8H).

Embodiment 18

Compound (I-18)

N-(5-(4-cycloheptylpiperazine-1-methyl)-pyridin-2-yl)-5-fluoro-4-(1-cyclobutyl-3-cyclopropyl-1H-indol-5-yl)pyrimidin-2-amine Compound I-18 was synthesized according to the method in Embodiment 1, and the starting materials were 1-cyclobutyl-3-cyclopropyl-5-(2-chloro-pyrimidin-4-yl)-1H-indole (its synthesis was similar to that in Embodiment 1, the starting materials were 2,4-dichloro-5-fluoro-pyrimidine and 1-cyclobutyl-3-cyclopropyl-5-boronic acid pinacol ester-1H-indole (the starting materials were bromocyclobutane and 3-cyclopropyl-5-bromo-1H-indole)) and 5-[(4-cycloheptylpiperazin-1-yl)methyl]pyridin-2-amine. The title product of N-(5-(4-cycloheptylpiperazine-1-methyl)-pyridin-2-yl)-5-fluoro-4-(1-cyclobutyl-3-cyclopropyl-1H-indol-5-yl)pyrimidin-2-amine (I-18) was obtained as a pale yellow solid. MS(m/z): 594 [M+H]$^+$. $^1$H NMR (DMSO-d$_6$): δ: 11.91 (br, 1H), 11.62 (br, 1H), 9.35 (s, 1H), 8.79-8.76 (m, 2H), 8.57 (s, 1H), 8.39-8.36 (m, 2H), 7.90-7.88 (d, J=8.0 Hz, 1H), 7.35 (s, 1H), 4.88-4.82 (m, 1H), 4.57 (s, 2H), 4.43-4.13 (m, 15H), 1.25-1.01 (m, 17H).

Embodiment 19

Compound (I-19)

N-(5-(4-cyclohexylpiperazin-1-methyl)-pyridin-2-yl)-5-fluoro-4-(1-cyclohexyl-3-cyclobutyl-1H-indol-5-yl)pyrimidin-2-amine Compound I-19 was synthesized according to the method in Embodiment 1, and the starting materials were 1-cyclohexyl-3-cyclobutyl-5-(2-chloro-pyrimidin-4-yl)-1H-indole (its synthesis was similar to that in Embodiment 1, and the starting materials were 2,4-dichloro-5-fluoro-pyrimidine and 1-cyclohexyl-3-cyclobutyl-5-boronic acid pinacol ester-1H-indole (the starting materials were bromocyclohexane and 3-cyclobutyl-5-bromo-1H-indole)) and 5-[(4-cyclohexylpiperazin-1-yl)methyl]pyridin-2-amine. The title product of N-(5-(4-cyclohexylpiperazine-1-methyl)-pyridin-2-yl)-5-fluoro-4-(1-cyclohexyl-3-cyclobutyl-1H-Indol-5-yl)pyrimidin-2-amine (I-19) was obtained as a pale yellow solid. MS(m/z): 622 [M+H]$^+$. $^1$H NMR (DMSO-d$_6$): δ: 11.92 (br, 1H), 11.63 (br, 1H), 9.37 (s, 1H), 8.80-8.78 (d, J=8.0 Hz, 1H), 8.57 (s, 1H), 8.39-8.36 (m, 2H), 7.90-7.88 (d, J=8.0 Hz, 1H), 7.67-7.65 (d, J=8.0 Hz, 1H), 7.37 (s, 1H), 4.83-4.68 (m, 3H), 4.60-4.56 (m, 1H), 4.45-4.11 (m, 15H), 1.27-1.01 (m, 20H).

Embodiment 20

Compound (I-20)

N-(5-(4-cyclopentylpiperazin-1-methyl)-pyridin-2-yl)-5-fluoro-4-(1-cycloheptyl-3-acetyl-1H-indol-5-yl)pyrimidin-2-amine Compound I-20 was synthesized according to the method in Embodiment 1, and the starting materials were 1-cycloheptyl-3-acetyl-5-(2-chloro-pyrimidin-4-yl)-1H-indole (its synthesis was similar to that in Embodiment 1, and the starting materials were 2,4-dichloro-5-fluoro-pyrimidine and 1-cycloheptyl-3-acetyl-5-boronic acid pinacol ester-1H-indole (the starting materials were bromocycloheptane and 3-acetyl-5-bromo-1H-indole)) and 5-[(4-cyclopentylpiperazin-1-yl)methyl]pyridin-2-amine. The title product of N-(5-(4-cyclopentylpiperazin-1-methyl)-pyridin-2-yl)-5-fluoro-4-(1-cycloheptyl-3-acetyl-1H-indol-5-yl)pyrimidin-2-amine (I-20) was obtained as a white solid. MS(m/z): 610 [M+H]$^+$. $^1$H NMR (DMSO-d$_6$): δ: 11.91 (br, 1H), 11.63 (br, 1H), 9.57 (s, 1H), 9.35 (s, 1H), 8.81-8.79 (d, J=8.0 Hz, 1H), 8.57 (s, 1H), 8.41-8.37 (m, 2H), 7.90-7.88 (d, J=8.0 Hz, 1H), 7.66-7.65 (d, J=4.0 Hz, 1H), 4.81-4.69 (m, 3H), 4.43-4.21 (m, 12H), 1.29-1.03 (m, 20H).

Embodiment 21

Compound (I-21)

N-(5-(4-cyclobutylpiperazin-1-yl)-pyridin-2-yl)-5-fluoro-4-(1-isopropyl-2-cyclopentyl-1H-indol-5-yl)pyrimidin-2-amine Compound I-21 was synthesized according to the method in Embodiment 1, and the starting materials were 1-isopropyl-2-cyclopentyl-5-(2-chloro-pyrimidin-4-yl)-1H-indole (its synthesis was similar to that in Embodiment 1, and the starting materials were 2,4-dichloro-5-fluoro-pyrimidine and 1-isopropyl-2-cyclopentyl-5-boronic acid pinacol ester-1H-indole (the starting materials were bromoisopropane and 2-cyclopentyl-5-bromo-1H-indole)) and 5-(4-cyclobutyrazin-1-yl)pyridin-2-amine. The title product of N-(5-(4-cyclobutylpiperazin-1-yl)-pyridin-2-yl)-5-fluoro-4-(1-isopropyl-2-cyclopentyl-1H-indol-5-yl)pyrimidin-2-amine (I-21) was obtained as a white solid. MS(m/z): 554 [M+H]$^+$. $^1$H NMR (DMSO-d$_6$): δ: 11.92 (br, 1H), 11.65 (br, 1H), 9.38 (s, 1H), 8.80-8.78 (d, J=8.0 Hz, 1H), 8.56 (s, 1H), 8.40-8.37 (m, 2H), 7.90-7.88 (d, J=8.0 Hz, 1H), 7.67-7.65 (d, J=8.0 Hz, 1H), 7.37 (s, 1H), 5.81-5.70 (m, 1H), 4.41-4.21 (m, 10H), 1.57-1.02 (m, 20H).

Embodiment 22

Compound (I-22)

N-(5-(4-ethylpiperazine-1-methyl)-pyridin-2-yl)-5-fluoro-4-(1-cyclopentyl-2-formic acid diformamido-1H-indol-5-yl)pyrimidin-2-amine Compound I-22 was synthesized according to the method in Embodiment 1, and the starting materials were 1-cyclopentyl-2-formic acid diformamido-5-(2-chloro-5-fluoropyrimidin-4-yl)-1H-indole and 5-[(4-ethylpiperazin-1-yl)methyl]pyridin-2-amine. The title product of N-(5-(4-ethylpiperazine-1-methyl)-pyridin-2-yl)-5-fluoro-4-(1-cyclopentyl-2-formic acid diformamido-1H-indol-5-yl)pyrimidin-2-amine (I-22) was obtained as a pale yellow solid. MS(m/z): 572 [M+H]$^+$. $^1$H NMR (DMSO-d$_6$): δ: 11.92 (br, 1H), 11.65 (br, 1H), 9.37 (s, 1H), 8.78-8.76 (d, J=8.0 Hz, 1H), 8.59 (s, 1H), 8.39-8.36 (m, 2H), 7.98-7.96 (m, 2H), 7.67-7.65 (d, J=8.0 Hz, 1H), 4.89-4.83 (m, 1H), 4.57 (s, 2H), 4.21 (s, 6H), 3.68-3.48 (m, 10H), 2.02-1.69 (m, 8H), 1.26-1.22 (t, J=8.0 Hz, 3H).

Embodiment 23

Compound (I-23)

N-(5-(piperazin-1-yl)-pyridin-2-yl)-5-fluoro-4-(1-isopropyl-2-acetyl-1H-indol-5-yl)pyrimidin-2-amine Compound I-23 was synthesized according to the method in Embodiment 1, and the starting materials were 1-isopropyl-2-acetyl-5-(2-chloro-5-fluoropyrimidin-4-yl)-1H-indole (its synthesis was similar to that in Embodiment 1, and the starting materials were 2,4-dichloro-5-fluoropyrimidine and 1-isopropyl-2-acetyl-5-boronic acid pinacol ester-1H-indole (the starting materials were bromoisopropane and 2-acetyl-5-bromo-1H-indole)) and 4-(6-aminopyridin-3-yl)piperazine-1-tert-butyl carboxylate. The title product of N-(5-(piperazin-1-yl)-pyridin-2-yl)-5-fluoro-4-(1-isopropyl-2-acetyl-1H-indol-5-yl)pyrimidin-2-amine hydrochloride (I-23) was obtained as a pale yellow solid. MS(m/z): 474 [M+H]+. 1H NMR (DMSO-d6): δ: 11.69 (br, 1H), 9.75 (br, 2H), 9.38 (s, 1H), 8.82 (s, 1H), 8.69-8.67 (d, J=8.0 Hz, 1H), 8.01-7.97 (m, 2H), 7.92 (s, 1H), 7.73-7.69 (m, 2H), 4.89-4.83 (m, 1H), 3.69-3.48 (m, 8H), 2.75 (s, 3H), 1.67-1.65 (d, J=8.0 Hz, 6H).

Embodiment 24

Compound (I-24)

N-(5-(4-ethylpiperazine-1-methyl)-pyridin-2-yl)-5-fluoro-4-(1-isopropyl-2-acetyl-1H-indol-5-yl)pyrimidin-2-amine Compound I-24 was synthesized according to the method in Embodiment 1, and the starting materials were 1-isopropyl-2-acetyl-5-(2-chloro-5-fluoropyrimidin-4-yl)-1H-indole and 5-[(4-ethylpiperazin-1-yl)methyl]pyridin-2-amine. The title product of N-(5-(4-ethylpiperazine-1-methyl)-pyridin-2-yl)-5-fluoro-4-(1-isopropyl-2-acetyl-1H-indol-5-yl)pyrimidin-2-amine (I-24) was obtained as a pale yellow solid. MS(m/z): 516[M+H]+. 1H NMR (DMSO-d6): δ: 11.93 (br, 1H), 11.67 (br, 1H), 9.36 (s, 1H), 8.78-8.76 (d, J=8.0 Hz, 1H), 8.58 (s, 1H), 8.39-8.36 (m, 2H), 7.98-7.95 (m, 2H), 7.67-7.65 (d, J=8.0 Hz, 1H), 4.89-4.82 (m, 1H), 4.58 (s, 2H), 3.68-3.51 (m, 10H), 2.67 (s, 3H), 1.67-1.65 (d, J=8.0 Hz, 6H), 1.27-1.23 (t, J=8.0 Hz, 3H).

Embodiment 25

Compound (I-25)

N-(5-(piperazin-1-yl)-pyridin-2-yl)-5-fluoro-4-(1-isopropyl-2-formic acid diformamido-1H-4-azaindol-5-yl)pyrimidin-2-amine Compound I-25 was synthesized according to the method in Embodiment 1, and the starting materials were 1-isopropyl-2-formic acid diformamido-5-(2-chloro-5-fluoropyrimidin-4-yl)-1H-4-azaindole (its synthesis was similar to that in Embodiment 1, and the starting materials were 2,4-dichloro-5-fluoropyrimidine and 1-isopropyl-2-formic acid diformamido-5-boronic acid pinacol ester-1H-4-azepine (the starting material were bromoisopropane and 2-formic acid diformamido-5-bromo-1H-4-azaindole)) and tert-butyl 4-(6-aminopyridin-3-yl)piperazine-1-carboxylate. The title product of N-(5-(piperazin-1-yl)-pyridin-2-yl)-5-fluoro-4-(1-isopropyl-2-formic acid diformamido-1H-4-azaindol-5-yl) pyrimidin-2-amine hydrochloride (I-25) was obtained as a pale yellow solid. MS(m/z): 504 [M+H]+. 1H NMR (DMSO-d6): δ: 11.69 (br, 1H), 9.77 (br, 2H), 9.39 (s, 1H), 8.82 (s, 1H), 8.69-8.67 (d, J=8.0 Hz, 1H), 8.01-7.98 (m, 1H), 7.92 (s, 1H), 7.73-7.69 (m, 1H), 6.87 (s, 1H), 4.82-4.51 (m, 15H), 1.67-1.65 (d, J=8.0 Hz, 6H).

Embodiment 26

Compound (I-26)

N-(5-(4-ethylpiperazine-1-methyl)-pyridin-2-yl)-5-fluoro-4-(1-isopropyl-2-formic acid diformamido-1H-4-azaindol-5-yl)pyrimidin-2-amine Compound I-26 was synthesized according to the method in Embodiment 1, and the starting materials were 1-isopropyl-2-formic acid diformamido-5-(2-chloro-5-fluoropyrimidin-4-yl)-1H-4-azaindole and 5-[(4-ethylpiperazin-1-yl)methyl]pyridin-2-amine. The title product of N-(5-(4-ethylpiperazine-1-methyl)-pyridin-2-yl)-5-fluoro-4-(1-isopropyl-2-formic acid diformamido-1H-4-azaindol-5-yl) pyrimidin-2-amine (I-26) was obtained as a pale yellow solid. MS(m/z): 546[M+H]+. 1H NMR (DMSO-d6): δ: 11.92 (br, 1H), 11.68 (br, 1H), 9.38 (s, 1H), 8.78-8.76 (d, J=8.0 Hz, 1H), 8.57 (s, 1H), 8.39-8.36 (m, 2H), 7.98-7.97 (m, 1H), 7.67-7.65 (d, J=8.0 Hz, 1H), 4.89-4.83 (m, 1H), 4.59 (s, 2H), 4.21 (s, 6H), 3.68-3.53 (m, 10H), 2.67 (s, 3H), 1.67-1.66 (d, J=4.0 Hz, 6H), 1.29-1.25 (t, J=8.0 Hz, 3H).

Embodiment 27

Compound (I-27)

N-(5-(4-ethylpiperazine-1-methyl)-pyridin-2-yl)-5-fluoro-4-(1-isopropyl-2-formic acid diformamido-1H-4-fluoroindol-5-yl)pyrimidin-2-amine Compound I-27 was synthesized according to the method in Embodiment 1, and the starting materials were 1-isopropyl-2-formic acid diformamido-5-(2-chloro-5-fluoropyrimidin-4-yl)-1H-4-fluoroindole and 5-[(4-ethylpiperazin-1-yl)methyl]pyridin-2-amine. The title product of N-(5-(4-ethylpiperazin-1-methyl)-pyridin-2-yl)-5-fluoro-4-(1-isopropyl-2-formic acid diformamido-1H-4-fluoroindol-5-yl)pyrimidin-2-amine (I-27) was obtained as a pale yellow solid. MS(m/z): 563 [M+H]+. 1H NMR (DMSO-d6): δ: 11.91 (br, 1H), 11.69 (br, 1H), 9.37 (s, 1H), 8.78-8.76 (d, J=8.0 Hz, 1H), 8.58 (s, 1H), 8.39-8.36 (m, 2H), 7.99-7.97 (d, J=8.0 Hz, 1H), 7.67-7.65 (d, J=8.0 Hz, 1H), 4.89-4.83 (m, 1H), 4.57 (s, 2H), 4.23 (s, 6H), 3.68-3.52 (m, 10H), 2.67 (s, 3H), 1.69-1.67 (d, J=4.0 Hz, 6H), 1.29-1.25 (t, J=8.0 Hz, 3H).

Embodiment 28

Compound (I-28)

N-(5-(piperazin-1-yl)-pyridin-2-yl)-5-fluoro-4-(1-isopropyl-2-formic acid diformamido-1H-4-fluoroindol-5-yl)pyrimidin-2-amine Compound I-28 was synthesized according to the method in Embodiment 1, and the starting materials were 1-isopropyl-2-formic acid diformamido-5-(2-chloro-5-fluoropyrimidin-4-yl)-1H-4-fluoroindole and tert-butyl 4-(6-aminopyridin-3-yl)piperazine-1-carboxylate. The title product of N-(5-(piperazin-1-yl)-pyridin-2-yl)-5-fluoro-4-(1-isopropyl-2-formic acid diformamido-1H-4-fluoroindol-5-yl)pyrimidin-2-amine hydrochloride (I-28) was obtained as a pale yellow solid. MS(m/z): 521[M+H]+. 1H NMR (DMSO-d6): δ: 11.67 (br, 1H), 9.76 (br, 2H), 9.41 (s, 1H), 8.85 (s, 1H), 8.69-8.67 (d, J=8.0 Hz, 1H), 8.00-7.98 (d, J=8.0 Hz, 1H), 7.92 (s, 1H), 7.73-7.69 (m, 2H), 4.89-4.82 (m, 1H), 4.77-4.62 (m, 14H), 1.68-1.66 (d, J=8.0 Hz, 6H).

Embodiment 29

Compound (I-29)

N-(5-(piperazin-1-yl)-pyridin-2-yl)-5-fluoro-4-(2-cyclopropyl-3-acetyl-2H-7-azaindazol-6-yl)pyrimidin-2-amine Compound I-29 was synthesized according to the method in Embodiment 1, and the starting materials were 2-cyclopropyl-3-acetyl-6-(2-chloro-5-fluoropyrimidin-4-yl)-2H-7-azaindazole (its synthesis was similar to that in Embodiment 1, and the starting materials were 2,4-dichloro-5-fluoropyrimidine and 2-cyclopropyl-3-acetyl-6-bromo-2H-7-azaindazole) and tert-butyl 4-(6-aminopyridin-3-yl)piperazine-1-carboxylate. The title product of N-(5-(piperazin-1-yl)-pyridin-2-yl)-5-fluoro-4-(2-cyclopropyl-3-acetyl-2H-7-azaindazol-6-yl)pyrimidin-2-amine hydrochloride (I-29) was obtained as a pale yellow solid. MS(m/z): 474 [M+H]$^+$. $^1$H NMR (DMSO-d$_6$): δ: 11.69 (br, 1H), 9.78 (br, 2H), 9.35 (s, 1H), 8.80-8.78 (d, J=8.0 Hz, 1H), 8.76 (s, 1H), 8.00-7.98 (d, J=8.0 Hz, 1H), 7.71-7.68 (m, 2H), 4.41-4.21 (m, 8H), 3.58-3.52 (m, 1H), 2.87 (s, 3H), 1.02-0.88 (m, 4H).

Embodiment 30

Compound (I-30)

N-(5-(piperazin-1-yl)-pyridin-2-yl)-5-fluoro-4-(2-methyl-3-isopropyl-2H-7-chloro-indazol-6-yl)pyrimidin-2-amine Compound I-30 was synthesized according to the method in Embodiment 1, and the starting materials were 2-methyl-3-isopropyl-7-chloro-6-(2-chloro-5-fluoropyrimidin-4-yl)-2H-indazole and tert-butyl 4-(6-aminopyridin-3-yl)piperazine-1-carboxylate. The title product of N-(5-(piperazin-1-yl)-pyridin-2-yl)-5-fluoro-4-(2-methyl-2H-7-chloro-indazol-6-yl)pyrimidin-2-amine hydrochloride (I-30) was obtained as a pale yellow solid. MS(m/z): 482 [M+H]$^+$. $^1$H NMR (DMSO-d$_6$): δ: 11.71 (br, 1H), 9.80 (br, 2H), 9.37 (s, 1H), 8.80-8.78 (d, J=8.0 Hz, 1H), 8.77 (s, 1H), 8.00-7.98 (d, J=8.0 Hz, 1H), 7.71-7.67 (m, 2H), 4.79 (s, 3H), 4.41-4.20 (m, 9H), 1.68-1.66 (d, J=8.0 Hz, 6H).

Embodiment 31

Compound (I-31)

N-(5-(piperazin-1-yl)-pyridin-2-yl)-5-fluoro-4-(2-methyl-3-formic acid diformamido-2H-7-fluoro-indazol-6-yl)pyrimidin-2-amine Compound I-31 was synthesized according to the method in Embodiment 1, and the starting materials were 2-methyl-3-formic acid diformamido-7-fluoro-6-(2-chloro-5-fluoropyrimidin-4-yl)-2H-indazole and tert-butyl 4-(6-aminopyridin-3-yl)piperazine-1-carboxylate. The title product of N-(5-(piperazin-1-yl)-pyridin-2-yl)-5-fluoro-4-(2-methyl-3-formic acid diformamido-2H-7-fluoro-indazol-6-yl) pyrimidin-2-amine hydrochloride (I-31) was obtained as a pale yellow solid. MS(m/z): 494 [M+H]$^+$. $^1$H NMR (DMSO-d$_6$): δ: 11.70 (br, 1H), 9.81 (br, 2H), 9.37 (s, 1H), 8.80-8.78 (d, J=8.0 Hz, 1H), 8.79 (s, 1H), 8.00-7.98 (d, J=8.0 Hz, 1H), 7.72-7.69 (m, 2H), 4.78 (s, 3H), 4.41-4.18 (m, 14H).

Embodiment 32

Compound (I-32)

N-(5-(piperazin-1-yl)-pyridin-2-yl)-5-fluoro-4-(1-acetyl-3-cyclopropyl-8-fluoro-imidazolo[1,5-a]pyridin-6-yl)pyrimidin-2-amine Compound I-32 was synthesized according to the method in Embodiment 1, and the starting materials were 1-acetyl-3-cyclopropyl-8-fluoro-6-(2-chloro-5-fluoropyrimidin-4-yl)-imidazolo[1,5-a]pyridin-6-yl)pyrimidine and 4-(6-aminopyridin-3-yl)piperazine-1-tert-butyl carboxylate. The title product of N-(5-(piperazin-1-yl)-pyridin-2-yl)-5-fluoro-4-(1-acetyl-3-cyclopropyl-8-fluoro-imidazolo[1,5-a]pyridin-6-yl)pyrimidin-2-amine hydrochloride (I-32) was obtained as a pale yellow solid. MS(m/z): 491[M+H]$^+$. $^1$H NMR (DMSO-d$_6$): δ: 11.71 (br, 1H), 9.79 (br, 2H), 9.71 (s, 1H), 9.38 (s, 1H), 8.21 (s, 1H), 7.79-7.75 (m, 2H), 7.21 (s, 1H), 4.32-4.20 (m, 8H), 2.79 (s, 3H), 2.01-1.51 (m, 5H).

Embodiment 33

Compound (I-33)

N-(5-(4-ethylpiperazine-1-methyl)-pyridin-2-yl)-5-fluoro-4-(3-trifluoromethyl-[1,2,4]triazolo[4,3-a]pyridin-6-yl)pyrimidin-2-amine Compound I-33 was synthesized according to the method in Embodiment 1, and the starting materials were 3-trifluoromethyl-6-(2-chloro-5-fluoropyrimidin-4-yl)-[1,2,4]triazolo[4,3-a]pyridine (its synthesis was similar to that in Embodiment 1, and the starting materials were 2,4-dichloro-5-fluoropyrimidine and 3-trifluoromethyl-6-bromo-[1,2,4]triazolo[4,3-a]pyridine) and 5-[(4-ethylpiperazin-1-yl)methyl]pyridin-2-amine. The title product of N-(5-(4-ethylpiperazine-1-methyl)-pyridin-2-yl)-5-fluoro-4-(3-trifluoromethyl-[1,2,4]triazolo[4,3-a]pyridin-6-yl)pyrimidin-2-amine (I-33) was obtained as a pale yellow solid. MS(m/z): 502[M+H]$^+$. $^1$H NMR (DMSO-d$_6$): δ: 11.91 (br, 1H), 11.63 (br, 1H), 9.68 (s, 1H), 9.38 (s, 1H), 8.83-8.79 (m, 2H), 8.45 (s, 1H), 7.80-7.78 (d, J=8.0 Hz, 1H), 7.02-7.00 (d, J=8.0 Hz, 1H), 4.55 (s, 2H), 3.58-3.42 (m, 10H), 1.28-1.24 (t, J=8.0 Hz, 3H).

Embodiment 34

Compound (I-34)

N-(5-(4-ethylpiperazine-1-methyl)-pyridin-2-yl)-5-fluoro-4-(3-cyano-imidazo[1,2-a]pyridin-6-yl)pyrimidin-2-amine Compound I-34 was synthesized according to the method in Embodiment 1, and the starting materials were 3-cyano-6-(2-chloro-5-fluoropyrimidin-4-yl)-imidazo[1,2-a]pyridine (its synthesis was similar to that in Embodiment 1, and the starting materials were 2,4-dichloro-5-fluoropyrimidine and 3-cyano-6-bromo-imidazo[1,2-a]pyridine) and 5-[(4-ethylpiperazin-1-yl)methyl]pyridin-2-amine. The title product of N-(5-(4-ethylpiperazine-1-methyl)-pyridin-2-yl)-5-fluoro-4-(3-cyano-imidazo[1,2-a]pyridin-6-yl)pyrimidin-2-amine (I-34) was obtained as a pale yellow solid. MS(m/z): 458 [M+H]$^+$. $^1$H NMR (DMSO-d$_6$): δ: 11.93 (br, 1H), 11.67 (br, 1H), 9.71 (s, 1H), 9.58 (s, 1H), 9.37 (s, 1H), 8.82-8.78 (m, 3H), 7.80-7.78 (d, J=8.0 Hz, 1H), 7.04-7.02 (d, J=8.0 Hz, 1H), 4.57 (s, 2H), 3.59-3.42 (m, 10H), 1.26-1.22 (t, J=8.0 Hz, 3H).

Embodiment 35

Compound (I-35)

N-(5-(4-ethylpiperazine-1-methyl)-pyridin-2-yl)-5-fluoro-4-(3-acetyl-[1,2,4]triazolo[4,3-a]pyridin-6-yl)pyrimidin-2-amine Compound I-35 was synthesized according to the method in Embodiment 1, and the starting materials were 3-acetyl- 6-(2-chloro-5-fluoropyrimidin-4-yl)-[1,2,4]triazolo[4,3-a]pyridine (its synthesis was similar to that in Embodiment 1, and the starting materials were 2,4-dichloro-5-fluoropyrimidine and 3-acetyl-6-bromo-[1,2,4]triazolo[4,3-a]pyridine) and 5-[(4-ethylpiperazin-1-yl)methyl]pyridin-2-amine. The title product of N-(5-(4-ethylpiperazine-1-methyl)-pyridin-2-yl)-5-fluoro-4-(3-acetyl-[1,2,4]triazolo[4,3-a]pyridin-6-yl)pyrimidin-2-amine (I-35) was obtained as a pale yellow solid. MS(m/z): 476 [M+H]$^+$. $^1$H NMR (DMSO-d$_6$): δ: 11.93 (br, 1H), 11.68 (br, 1H), 9.71 (s, 1H), 9.43 (s, 1H), 8.81-8.77 (m, 2H), 8.47 (s, 1H), 7.79-7.77 (d, J=8.0 Hz, 1H), 6.89-6.87 (d, J=8.0 Hz, 1H), 4.57 (s, 2H), 4.01 (s, 3H), 3.55-3.42 (m, 10H), 1.29-1.25 (t, J=8.0 Hz, 3H).

Embodiment 36

Compound (I-36)

N-(5-(4-ethylpiperazin-1-methyl)-pyridin-2-yl)-5-fluoro-4-(3-cyclopropyl-[1,2,4]triazolo[4,3-a]pyridin-6-yl)pyrimidin-2-amine Compound I-36 was synthesized according to the method in Embodiment 1, and the starting materials were 3-cyclopropyl-6-(2-chloro-5-fluoropyrimidin-4-yl)-[1,2,4]triazolo[4,3-a]pyridine (its synthesis was similar to that in Embodiment 1, and the starting materials were 2,4-dichloro-5-fluoropyrimidine and 3-cyclopropyl-6-bromo-[1,2,4]triazolo[4,3-a]pyridine) and 5-[(4-ethylpiperazin-1-yl)methyl]pyridin-2-amine. The title product of N-(5-(4-ethylpiperazine-1-methyl)-pyridin-2-yl)-5-fluoro-4-(3-cyclopropyl-[1,2,4]triazolo[4,3-a]pyridin-6-yl)pyrimidin-2-amine (I-36) was obtained as a pale yellow solid. MS(m/z): 474 [M+H]$^+$. $^1$H NMR (DMSO-d$_6$): δ: 11.91 (br, 1H), 11.69 (br, 1H), 9.69 (s, 1H), 9.39 (s, 1H), 8.80-8.76 (m, 2H), 8.45 (s, 1H), 7.78-7.76 (d, J=8.0 Hz, 1H), 6.89-6.87 (d, J=8.0 Hz, 1H), 4.56 (s, 2H), 3.58-3.47 (m, 10H), 2.02-1.57 (m, 8H).

Embodiment 37

Compound (I-37)

N-(5-(piperazin-1-yl)-pyridin-2-yl)-5-fluoro-4-(9-cyclopentyl-8-formic acid diformamido-9H-purin-2-yl)pyrimidin-2-amine Compound I-37 was synthesized according to the method in Embodiment 1, and the starting materials were 9-cyclopentyl-8-formic acid diformamido-2-(2-chloro-5-fluoropyrimidin-4-yl)-9H-purine (its synthesis was similar to that in Embodiment 8, and the starting materials were 2,4-dichloro-5-fluoropyrimidine and 9-cyclopentyl-8-formic acid diformamido-2-bromo-9H-purine) and 4-(6-aminopyridin-3-yl)piperazine-1-tert-butyl carboxylate. The title product of N-(5-(piperazin-1-yl)-pyridin-2-yl)-5-fluoro-4-(9-cyclopentyl-8-formic acid diformamido-9H-purin-2-yl)pyrimidin-2-amine hydrochloride (I-37) was obtained as a pale yellow solid. MS(m/z): 546[M+H]$^+$. $^1$H NMR (DMSO-d$_6$): δ: 11.75 (br, 1H), 11.60 (br, 1H), 9.83 (s, 1H), 9.36 (s, 1H), 8.82 (s, 1H), 8.00-7.96 (m, 2H), 4.89-4.83 (m, 1H), 4.33-4.28 (m, 4H), 3.61 (s, 6H), 3.15-3.06 (m, 4H), 2.77 (s, 3H), 2.30-2.18 (m, 8H).

Embodiment 38

Compound (I-38)

N-(5-(4-methylpiperazine-1-methyl)-pyridin-2-yl)-5-fluoro-4-(9-isopropyl-8-acetyl-9H-purin-2-yl)pyrimidin-2-amine Compound I-38 was synthesized according to the method in Embodiment 1, and the starting materials were 9-isopropyl-8-acetyl-2-(2-chloro-5-fluoropyrimidin-4-yl)-9H-purine (its synthesis was similar to that in Embodiment 8, and the starting materials were 2,4-dichloro-5-fluoropyrimidine and 9-isopropyl-8-acetyl-2-bromo-9H-purine) and 5-[(4-methylpiperazin-1-yl)methyl]pyridin-2-amine. The title product of N-(5-(4-methylpiperazin-1-methyl)-pyridin-2-yl)-5-fluoro-4-(9-isopropyl-8-acetyl-9H-purin-2-yl)pyrimidin-2-amine (I-38) was obtained as a pale yellow solid. MS(m/z): 505 [M+H]$^+$. $^1$H NMR (DMSO-d$_6$): δ: 11.92 (br, 1H), 11.62 (br, 1H), 9.83 (s, 1H), 9.37 (s, 1H), 8.85 (s, 1H), 8.04-8.02 (d, J=8.0 Hz, 1H), 7.03-7.01 (d, J=8.0 Hz, 1H), 5.88-5.83 (m, 1H), 4.59 (s, 2H), 4.51 (s, 3H), 4.23-4.04 (m, 11H), 2.24-2.23 (d, J=4.0 Hz, 6H).

Compound 39

Compound (I-39)

N-(5-(4-methylpiperazin-1-methyl)-pyridin-2-yl)-5-fluoro-4-(9-(3-pentyl)-8-isopropyl-9H-purin-2-yl)pyrimidin-2-amine Compound I-39 was synthesized according to the method in Embodiment 1, and the starting materials were 9-(3-pentyl)-8-isopropyl-2-(2-chloro-5-fluoropyrimidin-4-yl)-9H-purine (its synthesis was similar to that in Embodiment 8, and the starting materials were 2,4-dichloro-5-fluoropyrimidine and 9-(3-pentyl)-8-isopropyl-2-bromo-9H-purine) and 5-[(4-methylpiperazin-1-yl)methyl]pyridin-2-amine. The title product of N-(5-(4-methylpiperazine-1-methyl)-pyridin-2-yl)-5-fluoro-4-(9-(3-pentyl)-8-isopropyl-9H-purin-2-yl)pyrimidin-2-amine (I-39) was obtained as a pale yellow solid. MS(m/z): 533[M+H]$^+$. $^1$H NMR (DMSO-d$_6$): δ: 11.91 (br, 1H), 11.62 (br, 1H), 9.81 (s, 1H), 9.37 (s, 1H), 8.82 (s, 1H), 8.06-8.04 (d, J=8.0 Hz, 1H), 7.01-6.99 (d, J=8.0 Hz, 1H), 4.89-4.83 (m, 1H), 4.58-4.55 (m, 3H), 4.20-4.03 (m, 11H), 2.15-2.10 (m, 4H), 1.55-1.54 (d, J=4.0 Hz, 6H), 1.26-1.24 (d, J=8.0 Hz, 6H).

Embodiment 40

Compound (I-40)

N-(5-(4-ethylpiperazin-1-methyl)-pyridin-2-yl)-5-fluoro-4-(9-methyl-8-formic acid diformamido-9H-purin-2-yl)pyrimidin-2-amine Compound I-40 was synthesized according to the method in Embodiment 1, and the starting materials were 9-methyl-8-formic acid diformamido-2-(2-chloro-5-fluoropyrimidin-4-yl)-9H-purine (its synthesis was similar to that in Embodiment 8, and the starting materials are 2,4-dichloro-5-fluoropyrimidine and 9-methyl-8-formic acid diformamido-2-bromo-9H-purine) and 5-[(4-ethylpiperazin-1-yl)methyl]pyridin-2-amine. The title product of N-(5-(4-ethylpiperazine-1-methyl)-pyridin-2-yl)-5-fluoro-4-(9-methyl-8-formic acid diformamido-9H-purin-2-yl)

pyrimidin-2-amine (I-40) was obtained as a pale yellow solid. MS(m/z): 520[M+H]⁺. ¹H NMR (DMSO-d₆): δ: 11.91 (br, 1H), 11.62 (br, 1H), 9.83 (s, 1H), 9.39 (s, 1H), 8.84 (s, 1H), 8.02-8.00 (d, J=8.0 Hz, 1H), 7.00-6.98 (d, J=8.0 Hz, 1H), 4.89 (s, 3H), 4.58 (s, 2H), 4.22-4.02 (m, 16H), 1.28-1.24 (t, J=8.0 Hz, 3H).

Embodiment 41

Compound (I-41)

N-(5-(4-ethylpiperazine-1-methyl)-pyridin-2-yl)-5-fluoro-4-(6-acetyl-7-cyclopropyl-7H-pyrrolo[2,3-d]pyrimidin-4-yl)pyrimidin-2-amine Compound I-41 was synthesized according to the method in Embodiment 1, and the starting materials were 6-acetyl-7-cyclopropyl-4-(2-chloro-5-fluoropyrimidin-4-yl)-7H-pyrrolo[2,3-d]pyrimidine (its synthesis was similar to that in Embodiment 10, and the starting materials were 2,4-dichloro-5-fluoropyrimidine and 6-acetyl-7-cyclopropyl-4-bromo-7H-pyrrolo[2,3-d]pyrimidine) and 5-[(4-ethylpiperazin-1-yl)methyl]pyridin-2-amine. The title product of N-(5-(4-ethylpiperazine-1-methyl)-pyridin-2-yl)-5-fluoro-4-(6-acetyl-7-cyclopropyl-7H-pyrrolo[2,3-d]pyrimidin-4-yl)pyrimidin-2-amine (I-41) was obtained as a pale yellow solid. MS(m/z): 516 [M+H]⁺. ¹H NMR (DMSO-d₆): δ: 11.91 (br, 1H), 11.62 (br, 1H), 9.83 (s, 1H), 9.39 (s, 1H), 8.83 (s, 1H), 8.04-8.02 (d, J=8.0 Hz, 1H), 7.01-6.99 (d, J=8.0 Hz, 1H), 6.68 (s, 1H), 4.59 (s, 2H), 4.23-4.04 (m, 11H), 3.57 (s, 3H), 1.28-1.24 (t, J=8.0 Hz, 3H), 2.08-1.68 (m, 4H).

Embodiment 42

Compound (I-42)

N-(5-(4-ethylpiperazine-1-methyl)-pyridin-2-yl)-5-fluoro-4-(5-cyano-7-methyl-7H-pyrrolo[2,3-d]pyrimidin-4-yl)pyrimidin-2-amine Compound I-42 was synthesized according to the method in Embodiment 1, and the starting materials were 5-cyano-7-methyl-4-(2-chloro-5-fluoropyrimidin-4-yl)-7H-pyrrolo[2,3-d]pyrimidine (its synthesis was similar to that in Embodiment 10, and the starting materials were 2,4-dichloro-5-fluoropyrimidine and 5-cyano-7-methyl-4-bromo-7H-pyrrolo[2,3-d]pyrimidine) and 5-[(4-ethylpiperazin-1-yl)methyl]pyridin-2-amine. The title product of N-(5-(4-ethylpiperazin-1-methyl)-pyridin-2-yl)-5-fluoro-4-(5-cyano-7-methyl-7H-pyrrolo[2,3-d]pyrimidin-4-yl)pyrimidin-2-amine (I-42) was obtained as a pale yellow solid. MS(m/z): 473[M+H]⁺. ¹H NMR (DMSO-d₆): δ: 11.91 (br, 1H), 11.63 (br, 1H), 9.85 (s, 1H), 9.39 (s, 1H), 8.84 (s, 1H), 8.03-8.01 (d, J=8.0 Hz, 1H), 7.05 (s, 1H), 6.636.61 (d, J=8.0 Hz, 1H), 4.59 (s, 2H), 4.52 (s, 3H), 4.21-4.03 (m, 10H), 1.25-1.21 (t, J=8.0 Hz, 3H).

Embodiment 43

Compound (I-43)

N-(5-(piperazin-1-yl)-pyridin-2-yl)-5-fluoro-4-(1-cyclopentyl-3-formic acid diformamido-1H-indazol-5-yl)pyrimidin-2-amine Compound I-43 was synthesized according to the method in Embodiment 1, and the starting materials were 1-cyclopentyl-3-formic acid diformamido-5-(2-chloro-5-fluoropyrimidin-4-yl)-1H-indazole (its synthesis was similar to that in Embodiment 1, and the starting materials were 2,4-dichloro-5-fluoropyrimidine and 1-cyclopentyl-3-formic acid diformamido-5-bromo-1H-indazole (the starting materials were bromocyclopentane and 3-formic acid diformamido-5-bromo-1H-indazole)) and tert-butyl 4-(6-aminopyridin-3-yl)piperazine-1-carboxylate. The title product of N-(5-(piperazin-1-yl)-pyridin-2-yl)-5-fluoro-4-(1-cyclopentyl-3-formic acid diformamido-1H-indazol-5-yl)pyrimidin-2-amine hydrochloride (I-43) was obtained as a pale white solid. MS(m/z): 530 [M+H]⁺. ¹H NMR (DMSO-d₆): δ: 11.67 (br, 1H), 9.70 (br, 2H), 9.38 (s, 1H), 8.69-8.65 (m, 2H), 8.02-8.00 (d, J=8.0 Hz, 1H), 7.97 (s, 1H), 7.72-7.69 (m, 2H), 4.88-4.82 (m, 1H), 3.69-3.47 (m, 14H), 2.10-1.57 (m, 8H).

Embodiment 44

Compound (I-44)

N-(5-(4-ethylpiperazine-1-methyl)-pyridin-2-yl)-5-fluoro-4-(1-isopropyl-3-acetyl-1H-indazol-5-yl)pyrimidin-2-amine Compound I-44 was synthesized according to the method in Embodiment 1, and the starting materials were 1-isopropyl-3-acetyl-5-(2-chloro-5-fluoropyrimidin-4-yl)-1H-indazole (its synthesis was similar to that in Embodiment 1, and the starting materials were 2,4-dichloro-5-fluoropyrimidine and 1-isopropyl-3-acetyl-5-bromo-1H-indazole (the starting materials were bromoisopropane and 3-acetyl-5-bromo-1H-indazole)) and 5-[(4-ethylpiperazin-1-yl)methyl]pyridin-2-amine. The title product of N-(5-(4-ethylpiperazine-1-methyl)-pyridin-2-yl)-5-fluoro-4-(1-isopropyl-3-acetyl-1H-indazol-5-yl)pyrimidin-2-amine (I-44) was obtained as an off-white solid. MS(m/z): 517 [M+H]⁺. ¹H NMR (DMSO-d₆): δ: 11.90 (br, 1H), 11.69 (br, 1H), 9.38 (s, 1H), 8.80-8.77 (m, 2H), 8.50 (s, 1H), 8.04-8.02 (d, J=8.0 Hz, 1H), 7.79-7.77 (d, J=8.0 Hz, 1H), 6.88-6.86 (d, J=8.0 Hz, 1H), 4.65-4.60 (m, 1H), 4.56 (s, 2H), 3.59-3.47 (m, 10H), 2.79 (s, 3H), 1.69-1.67 (d, J=4.0 Hz, 6H), 1.29-1.25 (t, J=8.0 Hz, 3H).

Embodiment 45

Compound (I-45)

N-(5-(4-ethylpiperazine-1-methyl)-pyridin-2-yl)-5-fluoro-4-(1-cyclopentyl-3-methyl-4-fluoro-1H-indazol-5-yl)pyrimidin-2-amine Compound I-45 was synthesized according to the method in Embodiment 1, and the starting materials were 1-cyclopentyl-3-methyl-4-fluoro-5-(2-chloro-5-fluoropyrimidin-4-yl)-1H-indazole (its synthesis was similar to that in Embodiment 1, the starting materials were 2,4-dichloro-5-fluoropyrimidine and 1-cyclopentyl-3-methyl-4-fluoro-5-bromo-1H-indazole (the starting materials were bromocyclopentane and 3-methyl-4-fluoro-5-bromo-1H-indazole)) and 5-[(4-ethylpiperazin-1-yl)methyl]pyridin-2-amine. The title product of N-(5-(4-ethylpiperazine-1-methyl)-pyridin-2-yl)-5-fluoro-4-(1-cyclopentyl-3-methyl-4-fluoro-1H-indazol-5-yl)pyrimidin-2-amine (I-45) was obtained as a white solid. MS(m/z): 533 [M+H]⁺. ¹H NMR (DMSO-d₆): δ: 11.89 (br, 1H), 11.71 (br, 1H), 9.39 (s, 1H), 8.81-8.79 (d, J=8.0 Hz, 1H), 8.50 (s, 1H), 8.03-8.01 (d, J=8.0 Hz, 1H), 7.78-7.76 (d, J=8.0 Hz, 1H), 6.91-6.89 (d, J=8.0

Hz, 1H), 4.66-4.60 (m, 1H), 4.57 (s, 2H), 3.61-3.49 (m, 10H), 2.15-1.67 (m, 11H), 1.28-1.24 (t, J=8.0 Hz, 3H).

Embodiment 46

Compound (I-46)

N-(5-(4-ethylpiperazine-1-methyl)-pyridin-2-yl)-5-fluoro-4-(1-cyclopentyl-3-trifluoromethyl-4-aza-1H-indazol-5-yl)pyrimidin-2-amine Compound I-46 was synthesized according to the method in Embodiment 1, and the starting materials were 1-cyclopentyl-3-trifluoromethyl-4-aza-5-(2-chloro-5-fluoropyrimidin-4-yl)-1H-indazole (its synthesis was similar to that in Embodiment 1, and the starting materials were 2,4-dichloro-5-fluoropyrimidine and 1-cyclopentyl-3-trifluoromethyl-4-aza-5-bromo-1H-indazole (the starting materials were bromocyclopentane and 3-trifluoromethyl-4-aza-5-bromo-1H-indazole)) and 5-[(4-ethylpiperazin-1-yl)methyl]pyridin-2-amine. The title product of N-(5-(4-ethylpiperazine-1-methyl)-pyridin-2-yl)-5-fluoro-4-(1-cyclopentyl-3-trifluoromethyl-4-aza-1H-indazol-5-yl)pyrimidin-2-amine (I-46) was obtained as a white solid. MS(m/z): 570 [M+H]$^+$. $^1$H NMR (DMSO-d$_6$): δ: 11.88 (br, 1H), 11.68 (br, 1H), 9.38 (s, 1H), 8.80-8.78 (d, J=8.0 Hz, 1H), 8.51-8.47 (m, 2H), 8.03-8.01 (d, J=8.0 Hz, 1H), 6.90-6.88 (d, J=8.0 Hz, 1H), 4.67-4.60 (m, 1H), 4.58 (s, 2H), 3.62-3.53 (m, 10H), 2.10-1.67 (m, 8H), 1.26-1.22 (t, J=8.0 Hz, 3H).

Embodiment 47

Compound (I-47)

N-(5-(4-methylpiperazin-1-yl)-pyridin-2-yl)-5-fluoro-4-(9-isopropyl-8-methyl-9H-purin-2-yl)pyrimidin-2-amine Compound I-47 was prepared according to the methods in Embodiments 1 and 2, and 9-isopropyl-8-methyl-2-(2-chloro-5-fluoropyrimidin-4-yl)-9H-purine and 5-(4-methyl-piperazin-1-yl)pyridin-2-amine were used as starting materials to give the title product of N-(5-(4-methylpiperazin-1-yl)-pyridin-2-yl)-5-fluoro-4-(9-isopropyl-8-methyl-9H-purin-2-yl)pyrimidin-2-amine (I-47) as a pale yellow solid. MS(m/z): 463[M+H]$^+$. $^1$H NMR (DMSO-d$_6$): δ: 11.89 (br, 1H), 11.65 (br, 1H), 9.83 (s, 1H), 9.38 (s, 1H), 8.86 (s, 1H), 8.02-8.00 (d, J=8.0 Hz, 1H), 7.95-7.93 (d, J=8.0 Hz, 1H), 5.87-5.83 (m, 1H), 4.33-4.30 (m, 4H), 3.15 (s, 3H), 3.05-3.02 (m, 4H), 2.85 (s, 3H), 1.57-1.56 (d, J=4.0 Hz, 6H).

Embodiment 48

Compound (I-48)

N-(5-(4-ethylpiperazin-1-yl)-pyridin-2-yl)-5-fluoro-4-(9-isopropyl-8-methyl-9H-purin-2-yl)pyrimidin-2-amine Compound I-48 was prepared according to the methods in Embodiments 1 and 2, and 9-isopropyl-8-methyl-2-(2-chloro-5-fluoropyrimidin-4-yl)-9H-purine and 5-(4-ethyl-piperazin-1-yl)pyridin-2-amine were used as starting materials to give the title product of N-(5-(4-ethylpiperazin-1-yl)-pyridin-2-yl)-5-fluoro-4-(9-isopropyl-8-methyl-9H-purin-2-yl)pyrimidin-2-amine (I-48) as a pale yellow solid. MS(m/z): 477[M+H]$^+$. $^1$H NMR (DMSO-d$_6$): δ: 11.88 (br, 1H), 11.64 (br, 1H), 9.82 (s, 1H), 9.38 (s, 1H), 8.84 (s, 1H), 8.01-7.99 (d, J=8.0 Hz, 1H), 7.93-7.91 (d, J=8.0 Hz, 1H), 5.88-5.83 (m, 1H), 4.33-4.25 (m, 8H), 3.17 (s, 3H), 2.67-2.61 (q, J=8.0 Hz, 2H), 2.01-2.00 (d, J=4.0 Hz, 6H), 1.67-1.63 (t, J=8.0 Hz, 3H).

Embodiment 49

Biological Assays activity assay: The CDK4 protein kinase activity was measured using the Caliper mobility shift assay (see J. Biomol. Screen, 2009, PP31). The test compound was dissolved in DMSO and diluted with a kinase buffer solution (20 mM HEPES-pH 7.5, 0.01% Triton X-100, 10 mM MgCl$_2$, 2 mM DTT) and 5 μL of compound at 5-fold final concentration of reaction dissolved in 10% DMSO was added in a 384-well plate. The compound-free control well was 5 μL of 10% DMSO, and the no-activity control well was 5 μL of kinase buffer. 10 μL of a 2.5-fold diluted CDK4 enzyme solution (GST-CDK4(1-303 end)) was added and incubated at room temperature for 10 min, and then 10 μL of the 2.5-fold diluted substrate solution Peptide FAM-P8 was added. The reaction was stopped by adding 25 μL of stop solution after incubation at 28° C. for 3 h, and the conversion rate data was read on a Caliper EZ Reader II (Caliper Life Sciences) and the conversion rate was converted to inhibition rate data according to above method. Among them, the inhibition rate %=(max−conversion)/(max−min)×100%.

Activity Assay: The CDK6 protein kinase activity was measured using the Caliper mobility shift assay (see J. Biomol. Screen, 2009, PP31). The test compound was dissolved in DMSO and diluted with a kinase buffer solution (20 mM HEPES-pH 7.5, 0.01% Triton X-100, 10 mM MgCl$_2$, 2 mM DTT) and 5 μL of compound at 5-fold final concentration of reaction dissolved in 10% DMSO was added in a 384-well plate. The compound-free control well was 5 μL of 10% DMSO, and the no-activity control well was 5 μL of kinase buffer. 10 μL of a 2.5-fold diluted CDK6 enzyme solution (GST-CDK6(1-326 end)) was added and incubated at room temperature for 10 min, and then 10 μL of the 2.5-fold diluted substrate solution Peptide FAM-P8 was added. The reaction was stopped by adding 25 μL of stop solution after incubation at 28° C. for 3 h, and the conversion rate data was read on a Caliper EZ Reader II (Caliper Life Sciences) and the conversion rate was converted to inhibition rate data according to above method. Among them, the inhibition rate %=(max−conversion)/(max−min)×100%.

Results of above experiments are summarized in Table 2.

TABLE 2

| \multicolumn{6}{c}{Results of the assay} | | | | | |
|---|---|---|---|---|---|
| Compound | CDK4 | CDK6 | Compound | CDK4 | CDK6 |
| Palbociclib | D | D | I-1 | D | D |
| I-2 | D | D | I-3 | D | D |
| I-4 | D | C | I-5 | D | D |
| I-6 | D | C | I-7 | D | D |
| I-8 | D | C | I-9 | C | C |
| I-10 | D | C | I-11 | D | B |
| I-12 | D | D | I-13 | C | D |
| I-14 | D | D | I-15 | B | C |
| I-16 | D | D | I-17 | D | C |
| I-18 | D | D | I-19 | D | A |
| I-20 | D | D | I-21 | D | C |

TABLE 2-continued

Results of the assay

| Compound | CDK4 | CDK6 | Compound | CDK4 | CDK6 |
|---|---|---|---|---|---|
| I-22 | D | D | I-23 | D | D |
| I-24 | D | D | I-25 | D | D |
| I-26 | D | C | I-27 | D | D |
| I-28 | D | C | I-29 | D | D |
| I-30 | D | C | I-31 | D | D |
| I-32 | D | C | I-33 | D | D |
| I-34 | D | D | I-35 | C | C |
| I-36 | D | D | I-37 | D | C |
| I-38 | D | D | I-39 | D | D |
| I-40 | D | D | I-41 | D | D |
| I-42 | D | C | I-43 | D | D |
| I-44 | D | A | I-45 | C | C |
| I-46 | C | C | I-47 | D | C |
| I-48 | D | B | | | |

Note:
A represents $IC_{50} > 500$ nM, B represents 500 nM $\geq IC_{50} > 100$ nM, C represents 100 nM $\geq IC_{50} > 20$ nM, D represents $IC_{50} \leq 20$ nM.

What is claimed is:

1. A compound of Formula I:

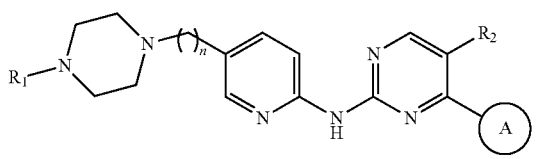

I or a pharmaceutically acceptable salt thereof,
wherein:

n is 0 or 1;

Ring A is selected from the group consisting of:

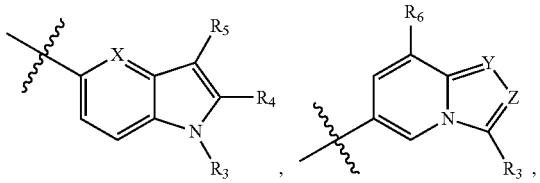

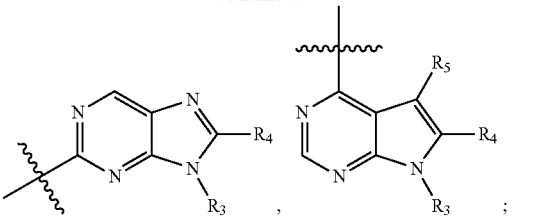

X is $CR_6$ or N;
Y is CH or N;
Z is CH or N;
$R_1$ is hydrogen, $C_1$-$C_3$ alkyl, or $C_3$-$C_7$ cycloalkyl;
$R_2$ is hydrogen, halogen, methyl, trifluoromethyl, or methoxy;
$R_3$ is $C_1$-$C_5$ alkyl or $C_3$-$C_7$ cycloalkyl;
$R_4$ is hydrogen, halogen, cyano, $C_1$-$C_3$ alkyl, trifluoromethyl, $C_3$-$C_5$ cycloalkyl, $C(O)CH_3$, or $C(O)NR_7R_8$;
$R_5$ is hydrogen, halogen, cyano, $C_1$-$C_3$ alkyl, trifluoromethyl, $C_3$-$C_5$ cycloalkyl, $C(O)CH_3$, or $C(O)NR_7R_8$;
$R_6$ is hydrogen or halogen;
$R_7$ is hydrogen or methyl; and
$R_8$ is hydrogen or methyl.

2. The compound according to claim 1, or a pharmaceutically acceptable salt thereof, wherein:
$R_1$ is methyl, ethyl, n-propyl, or isopropyl;
$R_3$ is methyl, ethyl, n-propyl, isopropyl, n-butyl, isobutyl, sec-butyl, tert-butyl, n-pentyl, 2-pentyl, 3-pentyl, 3-methyl-2-butyl, 1,1-dimethyl-1-propyl, or neopentyl;
$R_4$ is methyl, ethyl, n-propyl, or isopropyl; and
$R_5$ is methyl, ethyl, n-propyl or isopropyl.

3. The compound according to claim 1, or a pharmaceutically acceptable salt thereof, wherein:
$R_1$ is cyclopropyl, cyclobutyl, cyclopentyl, cyclohexyl, or cycloheptyl;
$R_2$ is fluoro, chloro, bromo, or iodo;
$R_3$ is cyclopropyl, cyclobutyl, cyclopentyl, cyclohexyl, or cycloheptyl;
$R_4$ is fluoro, chloro, bromo, iodo, cyclopropyl, cyclobutyl, or cyclopentyl;
$R_5$ is fluoro, chloro, bromo, iodo, cyclopropyl, cyclobutyl, or cyclopentyl; and
$R_6$ is fluoro, chloro, bromo, or iodo.

4. The compound according to claim 1, wherein the compound is selected from the group consisting of:

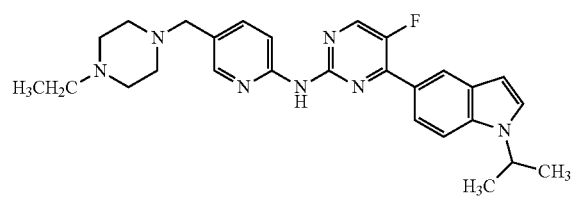

I-1

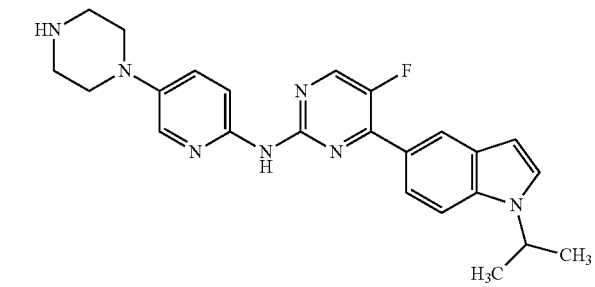

I-2

-continued
I-3
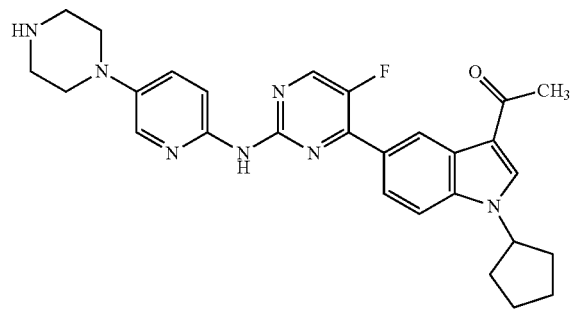
I-4
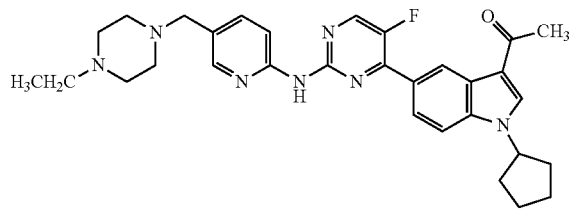
I-6
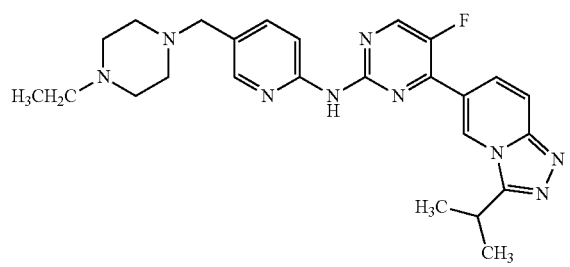
I-7
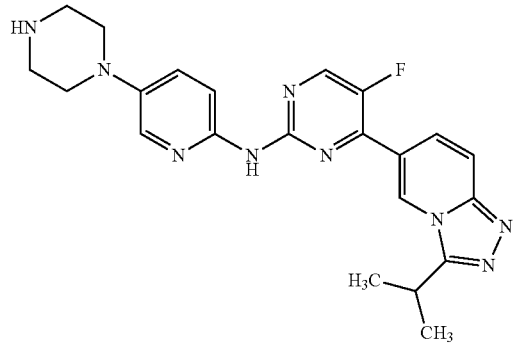
I-8
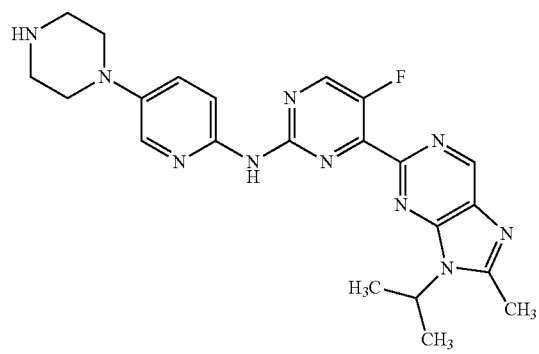
I-9
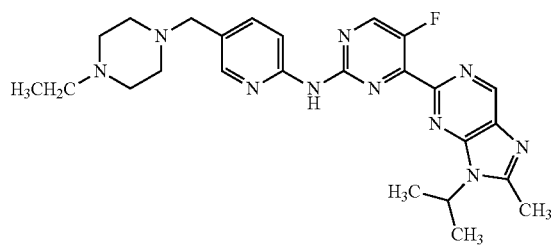
I-10
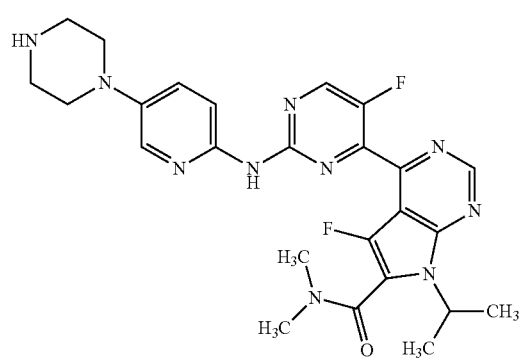
I-11
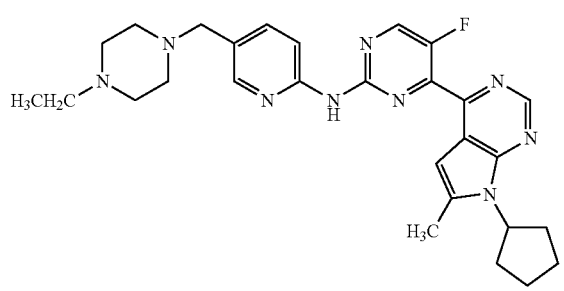

-continued
I-14
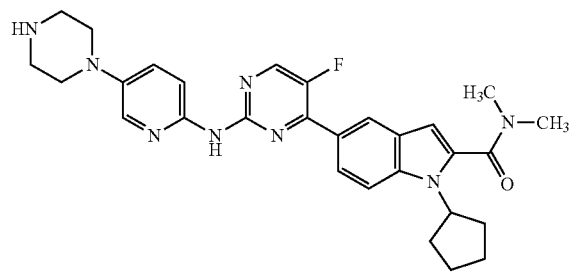
I-15
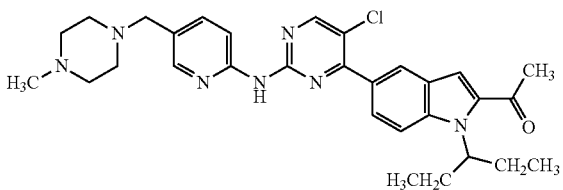
I-16
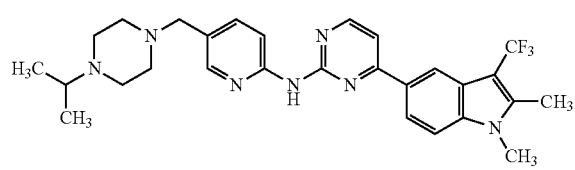
I-17
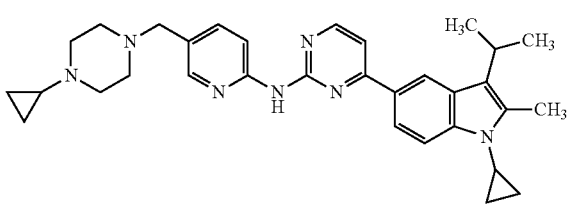
I-18
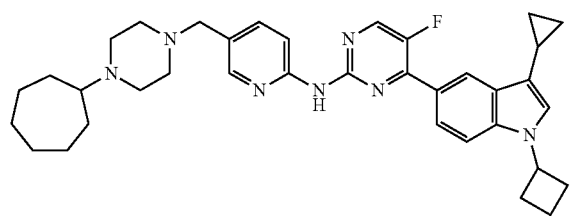
I-19
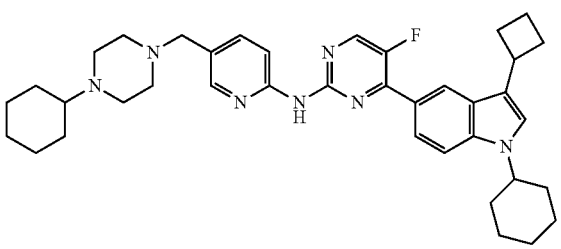
I-20
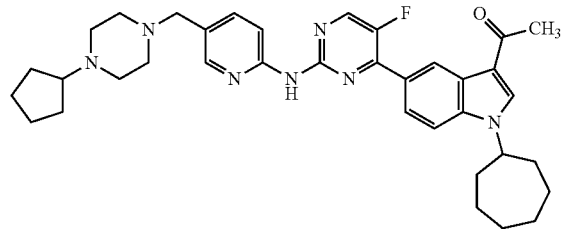
I-21
I-22
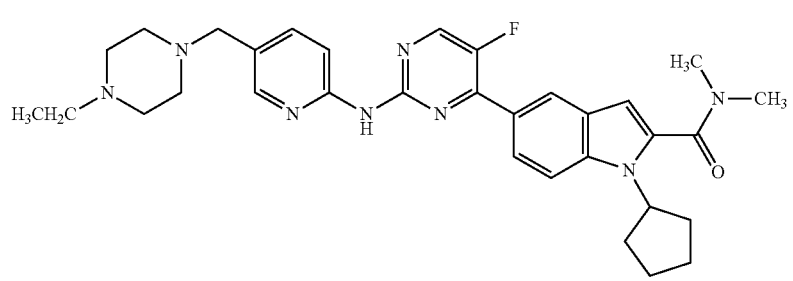

-continued
I-23
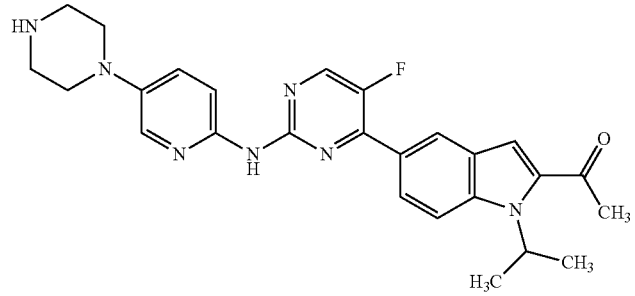
I-24
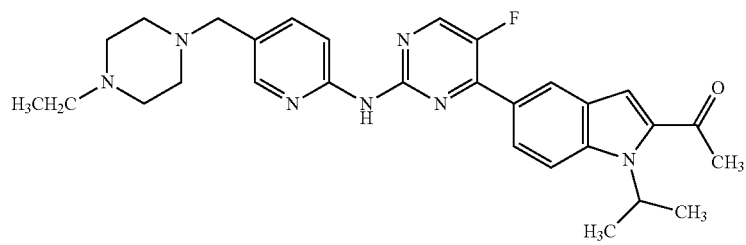
I-25
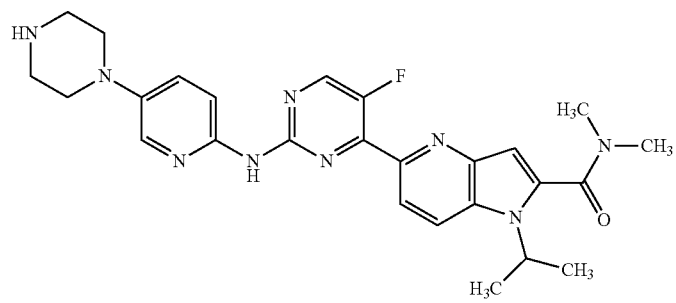
I-26
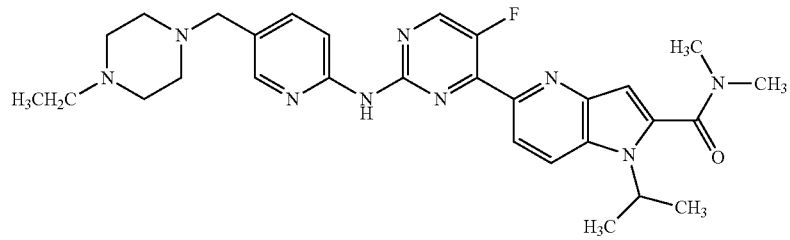
I-27
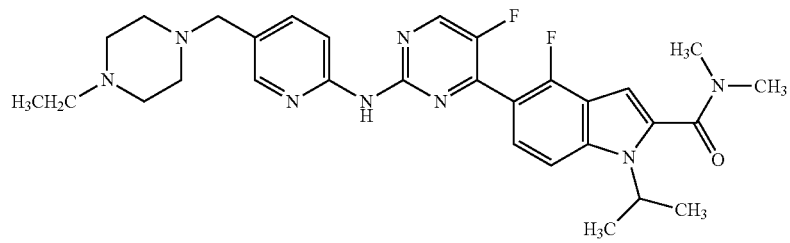

-continued
I-28
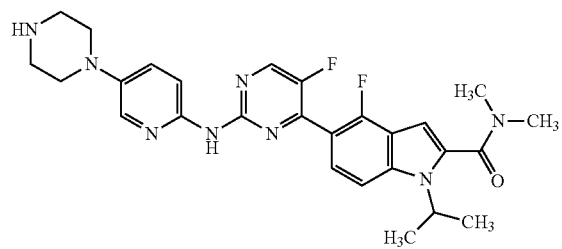
I-32
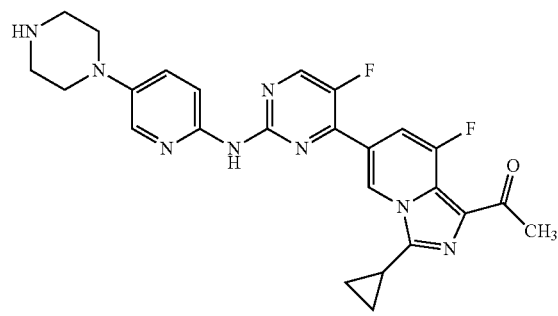
I-33
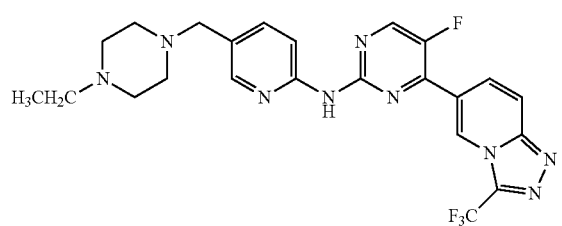
I-34
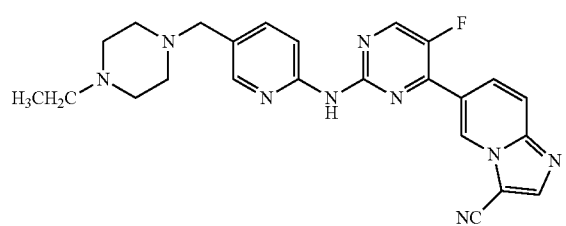
I-35
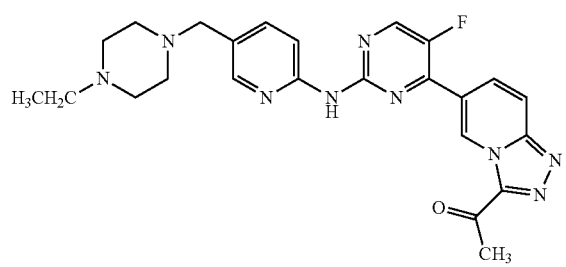
I-36
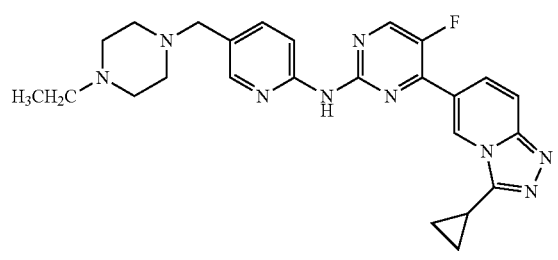
I-37
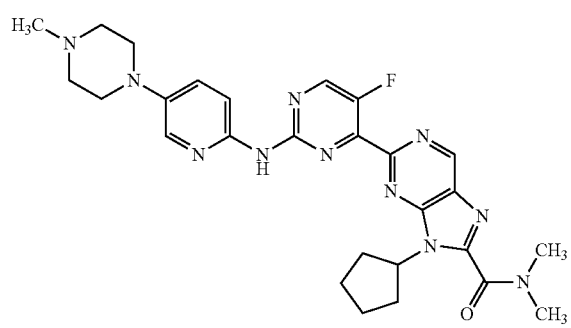
I-38
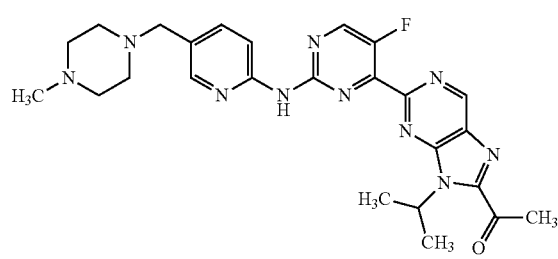
I-39
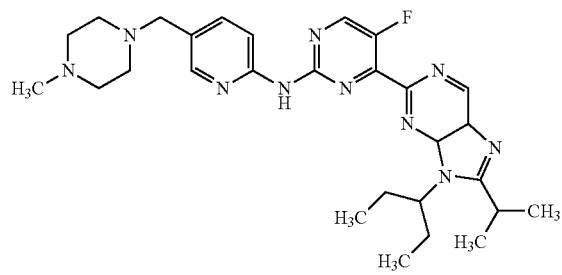
I-40

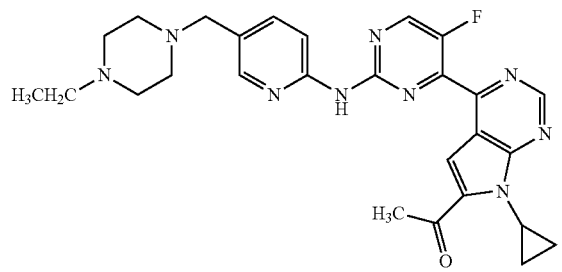

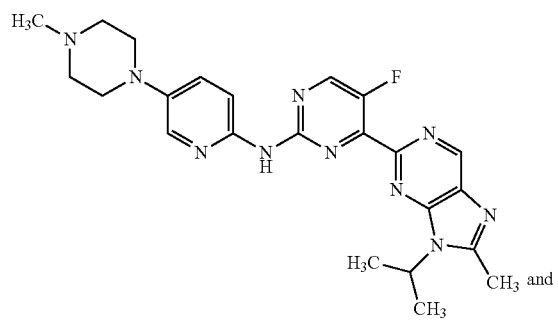

or a pharmaceutically acceptable salt thereof.

5. A pharmaceutical composition comprising a therapeutically effective amount of the compound according to claim 1, or a pharmaceutically acceptable salt thereof, and a pharmaceutically acceptable carrier or excipient.

6. A method for inhibiting cyclin-dependent kinase 4 activity or cyclin-dependent kinase 6 activity in a subject, comprising administering to the subject in need thereof a therapeutically effective amount of the compound according to claim 1, or a pharmaceutically acceptable salt thereof.

7. The method according to claim 6, wherein the subject has a cancer selected from the group consisting of melanoma, breast cancer, colorectal cancer, gastric cancer, liver cancer, ovarian cancer, pancreatic cancer, and prostate cancer.

* * * * *